US005863889A

United States Patent [19]

Benedict et al.

[11] Patent Number: 5,863,889

[45] Date of Patent: Jan. 26, 1999

[54] ICAM-1/LFA-1 SHORT-CHAIN PEPTIDES AND METHOD OF USING SAME

[75] Inventors: Stephen Benedict; Teruna J. Siahaan; Marcia A. Chan; Scott A. Tibbetts, all of Lawrence, Kans.

[73] Assignee: The University of Kansas, Lawrence, Kans.

[21] Appl. No.: 752,633

[22] Filed: Nov. 19, 1996

Related U.S. Application Data

[62] Division of Ser. No. 229,513, Apr. 19, 1994, abandoned.

[51] Int. Cl.[6] .......................... A61K 38/02; C07K 14/00; C07K 7/04

[52] U.S. Cl. .................................. 514/2; 514/12; 514/13; 530/300; 530/350; 530/324; 530/325; 530/326

[58] Field of Search .................................. 514/12, 13, 2; 530/300, 350

[56] References Cited

U.S. PATENT DOCUMENTS 5,340,800 8/1994 Lin et al. .................................. 514/12

FOREIGN PATENT DOCUMENTS 0 362 526 4/1990 European Pat. Off. .

OTHER PUBLICATIONS

Hynes, Cell 69, 11–25, 1992.

Stanley et al. EMBO J. 13, 1790–1798, 1994.

*Primary Examiner*—Stephen Walsh

*Assistant Examiner*—Nirmal S. Basi

*Attorney, Agent, or Firm*—Hovey,Williams, Timmons & Collins

[57] ABSTRACT

Short-chain peptides replicating fragments of functional domains derived from LFA-1 and ICAM-1 parent protein sequences serve to modulate the ICAM/LFA binding interaction. In one aspect of the invention, this modulation serves to block interprotein binding reactivity, as a peptide of the invention binds to a target protein in a manner that precludes the normal binding reaction between ICAM-1 and LFA-1. In another aspect of the invention, this modulation enhances the reactivity of a first peptide, as a second peptide induces a conformational change in the target protein from a first conformation to a second, more reactive, conformation. The peptides are used according to a method including the steps of providing the proteins and applying them to a population of cells.

18 Claims, 6 Drawing Sheets

ICAM-1/LFA-1 SHORT-CHAIN PEPTIDES AND METHOD OF USING SAME

This application is a division of application Ser. No. 08/229,513 filed Apr. 19, 1994 which application now abandoned.

SEQUENCE LISTING

A printed Sequence Listing accompanies this application,- and has also been submitted with identical contents in the form of a computer-readable ASCII file on a floppy diskette.

BACKGROUND OF THE INVENTION

1. Field of the Invention

The invention pertains to the field of protein chemistry and, more particularly, to short-chain peptides that serve to modulate interprotein interactions. More specifically, these short chain peptides have functional residue sequences that essentially replicate fragments of functional domain sequences in corresponding parent protein molecules, but without replicating the entire parent protein. A first such peptide may be mixed with a second peptide to enhance the functionality of the first peptide by inducing a conformational change in a target protein that is reactive with the first peptide. Similarly, the second peptide may induce a conformational change in the first peptide. Particularly preferred short-chain peptides are taken from parent protein molecule sequences selected from the family of integrins, proteins that react with integrins, and the superfamily of immunoglobulins. The peptides are utilized according to methods including the steps of providing the peptides and applying them to a population of cells.

2. Description of the Prior Art

Certain immune system functions rely upon a critical interprotein binding interaction as a necessary element of immune response. One such binding interaction pertains to a heterophilic interaction between the glycoproteins including Intercellular Adhesion Molecule ("ICAM-1") and Leucocyte Function Associated antigen-1 ("LFA-1"). Examples of published sequences for LFA-1 and ICAM-1 are submitted as Sequence ID No.'s 1, 2, and 3.

It is possible to derive immunological benefits by disrupting the intercellular ICAM/LFA binding interaction through the application of specific monoclonal antibodies ("mAbs"), i.e., anti-ICAM-1 or anti-LFA-1. As reported in Isobe et al., *Specific Acceptance of Cardiac Allograft After Treatment With Antibodies to ICAM*-1 and LFA-1, 255 SCIENCE 1125–1127 (Feb. 1992), an induced immune tolerance enables the indefinite survival of cardiac allografts between fully incompatible mouse strains subsequent to a six day treatment including the simultaneous application of anti-ICAM-1 and anti-LFA-1 mAbs. Unfortunately, a major problem with the use of mAbs for the purpose of inducing immune-tolerance in a mammal is that these large (e.g., 80–150 kDa) molecules typically also induce an effectiveness-limiting immune response to the mAbs.

LFA-1 has special significance in that it belongs to a family or class of proteins that are known as integrins, and is associated with leukocytes such as T and B cells. The integrin family includes similar glycoproteins that combine two separate protein units as a functional member, i.e., a functional heterodimer formed of a β unit and an α unit. These respective units each comprise separate proteins that are anchored within interactive proximity to one another, and can extend outwardly from a cytoplasmic domain, across a transmembrane domain, and beyond the cell membrane. In LFA-1, binding avidity for ICAM-1 involves $Mg^{2+}$ and $Ca^{2+}$ ions that, in part, govern the interaction between the β and α units.

The integrin family may be subdivided into two groups wherein common group members share common β units. A first group of proteins share the common β1 (CD29) unit, and typically function by binding to extracellular matrix proteins. This first group includes the VLA-1 (CD49a/CD29), VLA-2 (CD49b/CD29), VLA-3 (CD49c/CD29), VLA-4 (CD49d/CD29), VLA-5 (CD49e/CD29) and VLA-6 (CD49f/CD29) proteins. A second group shares the β2 unit (CD18), and typically functions in cell to cell interactions. This second group includes LFA-1 (CD18/CD11a), MAC-1 (CD18/CD11b), and p150,95 (CD18/CD11c). The LFA-1α unit (CD11a protein, i.e., Sequence ID No. 2) is the specific heterodimer counterpart to the β2 unit in LFA-1.

Li et al., *A Leukocyte Integrin Binding Peptide from Intercellular Adhesion Molecule*-2 *Stimulates T Cell Adhesion and Natural Killer Cell Activity,* 268 J. Biol. Chem. 21474-21477 (Jul. 20, 1993), report that β2 integrins, and particularly LFA-1, have a cytoplasmic domain which serves to alter protein configuration via a cellular phosphorylation pathway communicating the integrin and respective cell receptor areas. That is to say, phosphorylation may be activated at a remote receptor site with the result of indirectly inducing conformational changes in the integrin via cytoplasmic phosphorylation.

On the other hand, ICAM-1 proteins are not known to incur phosphorylation induced conformational changes. ICAM-1 is found primarily upon monocytes and endothelial cells, and is widely inducible, or upregulated, on many cells including B and T lymphocytes, thymocytes, dendritic cells, endothelial cells, fibroblasts, keratinocytes, chondrocytes, and epithelial cells. This protein has a co-stimulatory effect upon cytotoxic T-cell interaction, and is utilized in a number of intercellular binding interactions.

Recent developments in the field of protein chemistry confirm that short-chain peptides, which have amino acid residue sequences representing mere fragments of a corresponding parent protein molecule, may exhibit significant levels of biofunctionality. Short-chain peptides that derive from the ICAM-1 protein are known to have utility in blocking binding interactions between cells and viruses. Even so, only a very limited number of specific ICAM-1 based peptides have been shown to be useful.

European Patent Publication No. EP 391,088 A2 indicates that functional derivatives of the intercellular adhesion molecule ("ICAM-1") may be used in anti-viral therapy. These functional derivatives may include functional domains and fragments of the ICAM-1 molecule. The method of using these fragments includes administering them in a manner that prevents viral infection of potential viral host cells by impairing a binding interaction between the cells and rhinoviruses that may contact the cells. The binding interaction to be impaired includes one between an ICAM-1 cellular receptor and a corresponding viral adhesion site. The ICAM-1 fragments impair the cell-to-virus binding interaction by competing with normal cellular ICAM-1 molecules for adhesion to the corresponding viral binding site.

Another publication, PCT/AU91/00205, describes the use of short-chain ICAM-1 based peptides for inhibiting intercellular adhesion in mammals.

Summary of the Invention

The present invention overcomes the problems outlined above by providing, for methods of use, a variety of short-chain ICAM-1 and LFA-1 based peptides having sufficiently low molecular weights to avoid the induction of a mammalian immune system response of a type that would attack the peptides. These peptides are useful for modulating intercellular binding interactions by blocking or enhancing interprotein reactivity. In some instances, a single peptide can function as both a binding blocker or a binding enhancer, depending upon the peptide concentration. Another aspect of the invention pertains to the use of protein conformation modulator peptides that increase the avidity of these short-chain peptides for binding with naturally occurring ICAM-1 and LFA-1 based target proteins.

Peptides of the invention may have further utility in immunosuppression applications. A specific immune tolerance to organ transplants may be induced by killing T-cells that recognize the transplanted tissues as foreign antigens by mimicking the thymic winnowing of developing T-cells. Cytotoxic T-cells require a two-stage activation, which includes a first signal that results from contacting the T-cell antigen receptor with a specific antigen, and a second signal corresponding to for example the ICAM/LFA binding interaction. In the event that the second signal is blocked, the antigen-activated T-cell is eventually induced to die by apoptosis. Long-term immune tolerance is induced once the population of activatable antigen-specific T-cells dies. In a similar manner, these peptides may be used as an alternative treatment for various diseases where immunosuppression is a common therapy, e.g., Crohn's disease, ulcerative colitis, multiple sclerosis, rheumatoid arthritis, systemic lupus erythematosus, pemphigus vulgaris, pemphigoid, acquired epidermolysis bullous, allergic contact dermatitis, pyoderma gangrenosum, psoriasis, asthma, and diabetes.

Broadly speaking, one facet of the invention pertains to short-chain peptides that serve to promote the efficacy of other short-chain peptides in reacting with target proteins. It has been discovered that, in the case where a first short-chain peptide exhibits a specific type of biofunctionality, a second short-chain modulator peptide can induce conformational changes in a target protein, and these conformational changes can serve to increase the binding of the first protein for the target protein. The second peptide produces this increased level of binding by shifting the target protein from a first conformation to a second, more reactive conformation. Accordingly, a synergism is observed in that the first peptide has an increased level of reactivity with the target protein in the presence of the second peptide. A specific example of the use of modulator peptides includes the LFA-1β based LJCRF-4 (Sequence ID No. 16) peptide, which synergistically increases binding of the LFA-1α based LJCRF-6 (Sequence ID No. 18) peptide for binding with ICAM-1. Alternatively, these modulator peptides may induce a conformational change that decreases reactivity.

Short-chain peptides of the invention, e.g., Sequence ID Nos. 4–18, each preferably replicate a fragment of a functional domain that is based upon or identified from a parent protein molecule. These fragments have a residue sequence length less than the entire parent protein, and exhibit functionality as reactivity with naturally occurring proteins that are the reactive counterparts of the parent protein from which the peptides derive. By way of example, an ICAM-1 based peptide of the invention may consist essentially of the sequence from positions 28–37 of Sequence ID No. 3 (see Table 1). ICAM-1 based peptides compete with naturally occurring ICAM-1 proteins by targeting LFA-1 cellular proteins. Similarly, LFA-1 peptides target ICAM-1 cellular proteins.

These short-chain peptides exhibit biofunctionality as a capacity for modulating the natural ICAM/LFA binding interaction by either acting to block or enhance the level of protein interaction. This modulation results from ICAM-1 or LFA-1 based short-chain peptides that bind to a corresponding natural ICAM-1 or LFA-1 target protein on a cell. By way of example, in this bound position the short-chain peptide can serve to block a T-cell from attaching to another cell by precluding the LFA-1 or ICAM-1 to which the peptide is bound on one cell from interacting in the normal manner with a counterpart binding protein on the other cell.

A preferred form of the invention includes modulating the ICAM/LFA binding interaction by providing short-chain peptides that are based upon functional domain sub-sequences which are taken from the family of integrins. Sub-sequences that are taken from the LFA-1 α and β units are particularly preferred.

Short-chain peptides of the invention preferably have a molecular weight less than about 20 kDa, more preferably less than about 15 kDa, even more preferably less than about 10 kDa, and most preferably less than about 5 kDa, in order to reduce the chance for inducing an undesirable immune response, such as an allergic reaction or the production of antibodies for attacking the peptides, which might otherwise occur after the peptides are injected into a mammal or other organism. Alternatively, peptides of the invention preferably have an amino acid residue sequence of a length less than about 50 residues, more preferably have a length less than about 30 residues, and most preferably have a length less than about 25 residues.

In a study of the ICAM/LFA interaction, the degree of peptide binding to a target protein can be acceptably quantified by using a flow cytometer to measure median fluorescence intensity peak shifts in terms of percentage change from a control peak. In this type of device, a population of cells is individually subjected to a laser fluorescence study for purposes of identifying the presence of fluorescein labeled peptides that previously bound to a target protein on a living cell. The fluorescence intensity results for each cell are plotted in the general shape of a bell curve, and a median intensity peak value is calculated for the test sample as well as a control sample. Median peak shifts greater than about 10% with respect to the control usually indicate a level of functionality beyond that which might be induced by mere laboratory error, and shifts greater than about 20% are particularly good indicators of modulation in the ICAM/LFA binding interaction.

The peptides are used by introducing them into a population of cells. A blocking peptide can be mixed with a modulator peptide for increased in vivo efficacy of the blocking peptide.

Peptides of the invention may be produced by any available method including, by way of example, automated protein synthesis and recombinant host expression.

DETAILED DESCRIPTION OF THE PREFERRED EMBODIMENT

Figure 1:
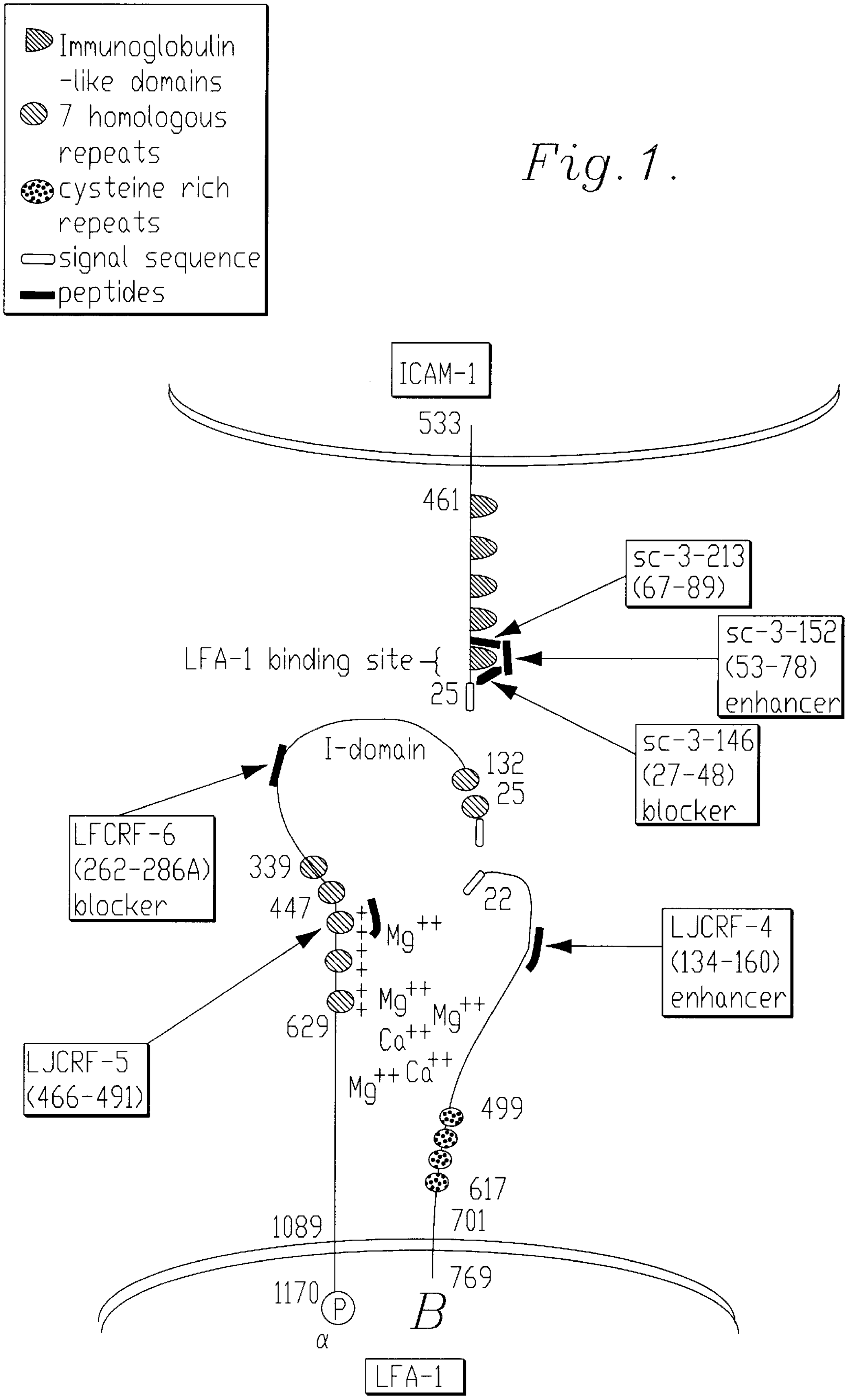
FIG. 1 schematically depicts the LFA-1 and ICAM-1 proteins, including special regions of interest such as signal sequences, sequence repeat regions, and suspected functional domains from which short-chain peptides were selected for synthetic replication.

The following examples provide, by way of example, specific methodology that may be utilized to practice preferred forms of the invention.

EXAMPLE 1

Short Chain Polypeptide Identification and Synthesis

Table 1 below identifies synthetically produced amino acid residue sequences replicating functional domain polypeptide fragments from the parent proteins (LFA-1 and ICAM-1) upon which they are based. Parent protein amino acid residue sequences of the integrin LFA-1 include the β or CD18 subunit (Sequence ID NO. 1) and the α or CD11a subunit (Sequence ID NO. 2). The ICAM-1 or CD54 (Sequence ID NO. 3) sequence was used as another parent protein.

These functional domains were selected to include suspected ICAM/LFA interprotein binding sites. The fragments were arbitrarily selected in sub-regions over the domains of interest as short-chain sequences for synthetic replication, with each sequence having no more than about 30 amino acid residues, in order to reduce the molecular weight and reduce the chance of provoking an immune system response in mammals injected with the peptides. These selected sequences are identified as Sequence ID Nos. 4–15 in Table 1. In particular, the synthetic peptides reproduced sub-regions of Sequence ID No. 3 within positions 25–95, and these respective sub-regions randomly overlapped. Other parent protein regions included positions 130–160 of Sequence ID No. 1, as well as Sequence ID No. 2 positions 260–290 and 465–495.

Table 1 provides a specific positional cross-reference between the synthetic peptide sequences and the parent protein sequences according to the Sequence Listing. Those synthetic peptide sequences having a designation including a "LJCRF" prefix were synthesized on commercial order by La Jolla Cancer Research Foundation of La Jolla, Calif. using a Model 430A peptide synthesizer (manufactured by ABI of Foster City, Calif.). This entire peptide synthesis was conducted according to standard solid phase protocols employing t-butyloxy-carbamate amino acid chemistry; i.e., standard techniques described in Atherton and Sheppard, *Solid Phase Peptide Synthesis*, which generally follow the protein synthesis techniques as identified in Merrifield, *Automated Synthesis of Peptides,* 150 Science 178–185 (Oct. 1965). The remaining sequences were synthesized according to the same protocols at the University of Kansas, Department of Pharmaceutical Chemistry, in Lawrence, Kans.

TABLE 1

SHORT CHAIN SYNTHETIC PEPTIDES AND SEQUENCE LISTING COMPARISON TO NATURAL PROTEINS

| Designation | Sequence ID | Residue Length | Positional Comparison to |
|---|---|---|---|
| ICAM (CD54) Based Peptides | | | Sequence ID NO. 3 |
| TJS-1-149A | 4 | 21 | 28–48 (Cys at position 48 of Sequence ID NO. 3 is Gly at position 21 of Sequence ID NO. 4) |
| SC-1-232 | $5_a$ | 22 | 28–48 |
| LJCRF-1 (SC-3-146) | 6 | 21 | 28–48 (Cys at position 48 of Sequence ID NO. 3 is Gly at position 21 of Sequence ID NO. 4) |
| SC-3-150 | 7 | 12 | 37–48 (Ile at position 37 of Sequence ID NO. 3 is Cys at position 1 of Sequence ID No. 7) |
| RB-1-51 | $8_b$ | 12 | 37–48 (Ile at position 37 of Sequence ID NO. 3 is Cys at position 1 of Sequence ID No. 8) |
| MC-1-80 | 9 | 11 | 38–48 (Cys at position 48 of Sequence ID NO. 3 is Gly at position 11 of Sequence ID NO. 9) |
| SC-3-111 | 10 | 10 | 28–37 |
| LJCRF-2 (SC-3-213) | 11 | 25 | 53–77 |
| LJCRF-3 | 12 | 24 | 67–90 |
| LJCRF-7 | 13 | 10 | 33–42 |
| LJCRF-8 | $14_c$ | 12 | 33–43 |
| RB-1-52 | $15_{b,c}$ | 12 | 33–43 |
| LFA-1 β (CD18) Based Peptides | | | Sequence ID NO. 1 |
| LJCRF-4 | 16 | 25 | 134–159 (Met at position 139 of Sequence ID NO. 1 was not synthetically reproduced because of the problem with oxidation of Met) |
| LFA-1 α (CD 11a) Based Peptides | | | Sequence ID NO. 2 |
| LJCRF-5 | 17 | 24 | 466–491 (Leu Leu at positions 478 and 479 of Sequence ID No. 2 were not synthetically reproduced because of the problem of synthesizing three Leu in a row) |
| LJCRF-6 | 18 | 24 | 262–286 (Arg at position 281 of Sequence ID NO. 2 was not synthetically reproduced because the first attempt at synthesis had difficulty in replicating this residue) |

TABLE 1-continued

| SHORT CHAIN SYNTHETIC PEPTIDES AND SEQUENCE LISTING COMPARISON TO NATURAL PROTEINS | | | |
|---|---|---|---|
| Designation | Sequence ID | Residue Length | Positional Comparison to |
| RB-1-88 | 19d | 24 | 262–286 (Arg at position 281 of Sequence ID NO. 2 was not synthetically reproduced because the first attempt at synthesis had difficulty in replicating this residue) |

NOTES:
a — Xaa is coumarin.
b — Cyclic peptide having a disulfide bond between Cys and/or Pen residues formed by dropwise addition of 2% (aquequs) potassium ferricyanide solution to a dilute solution of their respective linear peptides at pH 7.8.
c — Xaa is penicillamine.
d — Xaa is fluorescein isothiocyanate.

EXAMPLE 2

Antibody Binding Assay

An antibody binding assay was performed to demonstrate that peptides of the invention can change the ability of anti-LFA-1 and anti-ICAM-1 mAbs to bind with to human T-cells. The T-cells were selected as Molt3 cells, a leukemia-derived human T-cell line that was purchased from American Type Culture Collection of Rockville, Maryland, and which had a catalog number CRL-1552.

A 1 ml quantity of the Molt3 inoculum was warmed to 37° C. and transferred by pipette into about 25 ml of a growth culture medium including RPMI 1640 lymphocyte growth medium (Fisher Scientific of St. Louis, Miss.) mixed with 10% by volume fetal calf serum, 100 units/ml penicillin, 100 μg/ml streptomycin and 2 mM glutamine. The inoculated culture was incubated for three to four days at 37° C. under a normal atmosphere having about 5% $CO_2$ added thereto. This culture was capable of being maintained indefinitely by siphoning away the top (non-cell containing) layer and adding 50 ml (or more) of growth culture medium at intervals of three to four days.

An aqueous buffer solution including Dulbecco's phosphate buffered saline and bovine serum albumin ("-PBS/BSA solution") was prepared for use, and included a mixture of 200 mg $KH_2PO_4$, 1.15 g $Na_2HPO_4$, 100 mg $CaCl_2$, 200 mg KCl, 100 mg $MgCl_2.6H_2O$, 8 g NaCl, with distilled water added to a final 1 liter volume at room temperature, thus, forming a "PBS" solution of pH 7.4 to which was added 0.5% by weight bovine serum albumin.

An aliquot of about 7 ml was removed from the incubated culture medium and subjected to washing with the PBS/BSA solution. The washing procedure was initiated by placing the aliquot in a centrifuge (Model GT422 from Jouan, distributed Piruscio & Assoc. of Manchester, Miss.) at 1400 rpm for 6.5 minutes to separate the cells from the growth medium. The supernatant fluid was decanted, a 5 ml portion of PBS/BSA solution was transferred by pipette into the pellet, and the mixture was again centrifuged as before. The resulting supernatant fluid was decanted and the cells from the pellet were resuspended in PBS/BSA solution at a titer of about $1\times10^6$ cells/ml. A 500 μl portion of the solution containing the resuspended cells was placed in a microcentrifuge (Marathon 13K/M from Fisher Scientific of St. Louis, Miss.) at 3500 rpm for six minutes, to provide a washed pellet.

The washed pellet was resuspended in a 25 μl peptide cocktail including PBS solution mixed with 455 nmol of the LJCRF-1 peptide described in Table 1 above. The cells were incubated with the peptide cocktail at 37° C. for 45 minutes.

After incubation with the peptide cocktail, several antibodies were successively mixed into the incubated solution. A 75 μl portion of anti-IgM solution (a mixture of 10 μl of goat anti-human IgM stock purchased from Jackson Immuno Research of Westgrove, Pa.; and 65 μl of PBS/BSA solution) was added to the peptide cocktail for blocking of nonspecific binding of the secondary antibody. The resulting mixture was incubated for 10 minutes on ice. About 0.1 μg of a primary antibody including mouse IgG anti-human CD11a (purified according to conventional protocols at the University of Kansas Department of Pharmacology and Toxicology from an American Type Culture hybridoma cell line having Catalogue Number HB-202) was next stirred into the mixture, which was then incubated for 30 minutes at room temperature. The incubated mixture was placed in a microcentrifuge at 3500 rpm for six minutes to remove the cells from the mixture, and the cell pellet was washed two times by adding 500 μl aliquots of PBS/BSA solution and microfuging to remove non-bound antibodies from the cells as before. The resulting washed pellet was resuspended in 100 μl of a secondary antibody cocktail including 5 μl of fluorescein isothiocyanate ("FITC") labeled goat anti-mouse IgG (from CALTAG of South San Francisco, Calif.) and 95 μl of PBS/BSA solution. The resulting solution was incubated for 30 minutes at room temperature in the dark.

The incubated solution including the secondary antibody cocktail was microfuged at 3500 rpm for six minutes to remove the cells from the solution, and the cell pellet was washed two times with 500 μl portions of PBS/BSA solution, as before, to remove unbound antibodies. The washed pellet was resuspended in 500 μl of PBS/BSA solution, and the mixture was assayed in a flow cytometer (FACscan from Becton-Dickinson of San Jose, Calif.) to obtain a fluorescein fluorescence intensity analysis at 520 nm following laser excitation of the individual cells at 488 nm.

Identical peptide assays to that described above were conducted for several of the synthetic peptides listed in Table 1, using respective 455 nmol amounts of each peptide in the corresponding peptide cocktails. In these additional assays, mouse IgG anti-human CD54 (purchased from Cambridge Research Biochemicals of Wilmington, Del.) was substituted for the primary antibody in each instance where the peptide was based on an LFA-1 positional reference.

Figure 2:
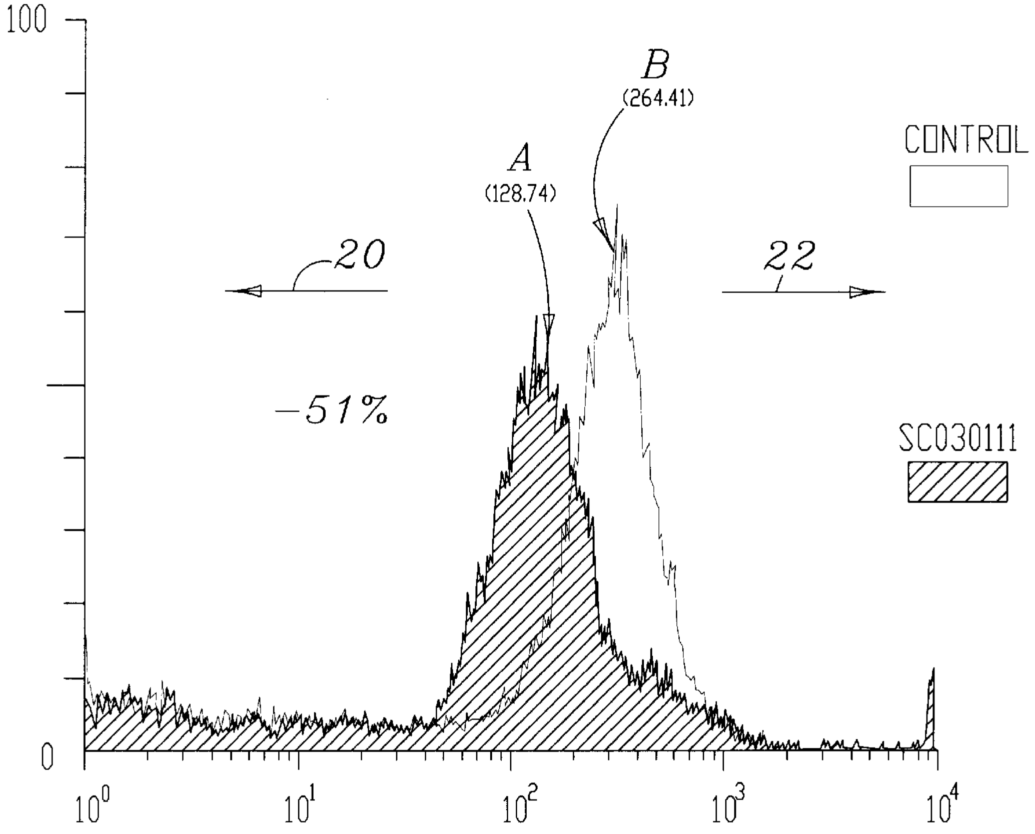
FIG. 2 depicts a Cartesian plot of flow cytometer results that were obtained from one of several fluorescence runs that were conducted to quantify the capacity of the ICAM-1 based SC-3-111 (Sequence ID No. 10) peptide for blocking the specific antibody binding of anti-LFA-1 mAb.
Figure 3:
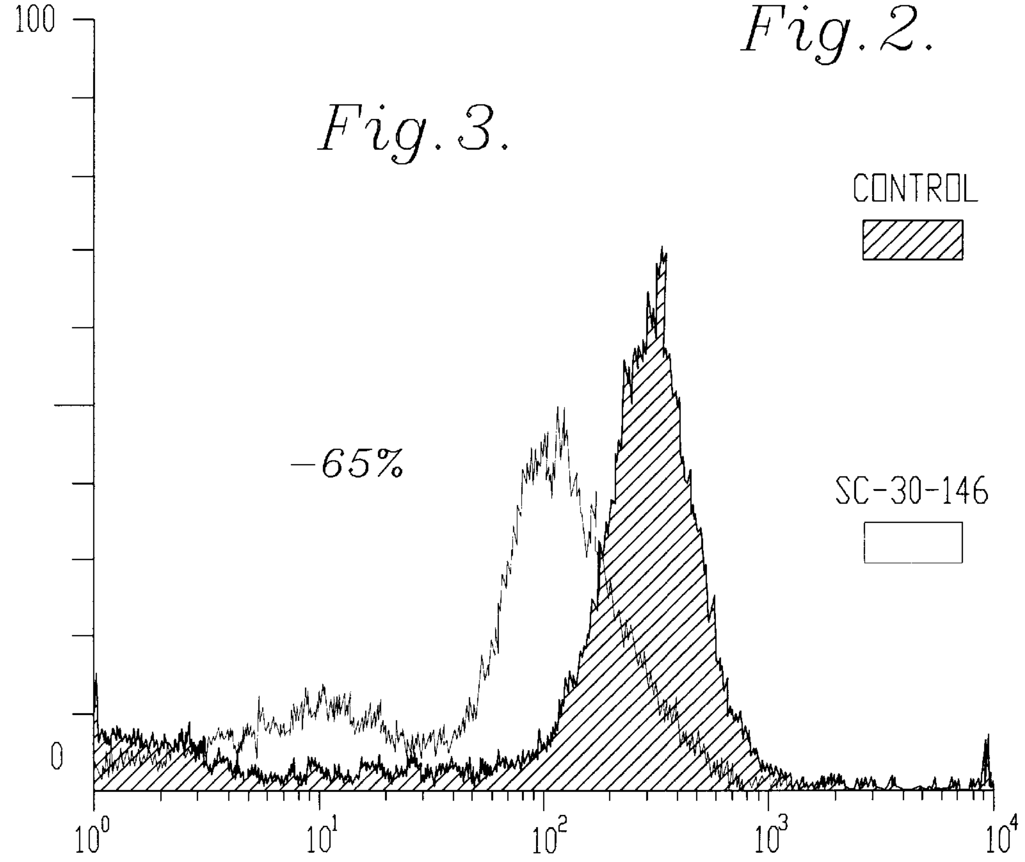
FIG. 3 is a plot similar to FIG. 2, but derived from a sample of the LJCRF-1 (Sequence ID No. 6) peptide.

The FACscan computer was used to calculate the relative amount of antibody bound per cell using the computer generated median of the peak. FIGS. 2 and 3 provide sample curves produced by this instrumentation, and each includes a two dimensional plot of fluorescence intensity (x axis) versus relative number of cells (y axis) for the synthetic peptides SC-3-111 (Sequence ID No. 10 corresponding to an above average 51% blocking efficiency at a 4550 μM concentration) and LJCRF-1 (Sequence ID No. 6 corresponding to an above average 65% blocking efficiency at 4550 μM).

In FIG. 2, by way of example, a first SC-3-111 (Sequence ID No. 10) peptide sample median peak value at A has an intensity value of 128.74. A control sample was obtained from an identical procedure to that of the SC-3-111 (Sequence ID No. 10) sample, but one without the step of adding a synthetic peptide cocktail. A control sample median peak value at B has an intensity value of 264.41. Accordingly, shifting of Peak A away from Peak B in the direction of arrow 20 indicates, by a reduction of cell fluorescence intensity values, that less mouse IgG anti-human CD11a is specifically bound to the T-cells. The degree of shifting was quantified by applying a calculation for percentage change:

% change=[(observed−control/(control)]*100; i.e.,

% change=[(128.74−264.41)/(264.41)]*100%=−51%.

The shifting of Peak A in the negative direction of arrow 20 indicates successful antibody blocking, i.e., the peptides modulated the antibody to T-cell binding interaction by inhibiting or blocking the antibody from attaching to its complimentary LFA or ICAM target. Similarly, a shifting of Peak A in the opposite (positive) direction of arrow 22 would indicate an enhanced level of binding as compared to the control.

Figure 4:
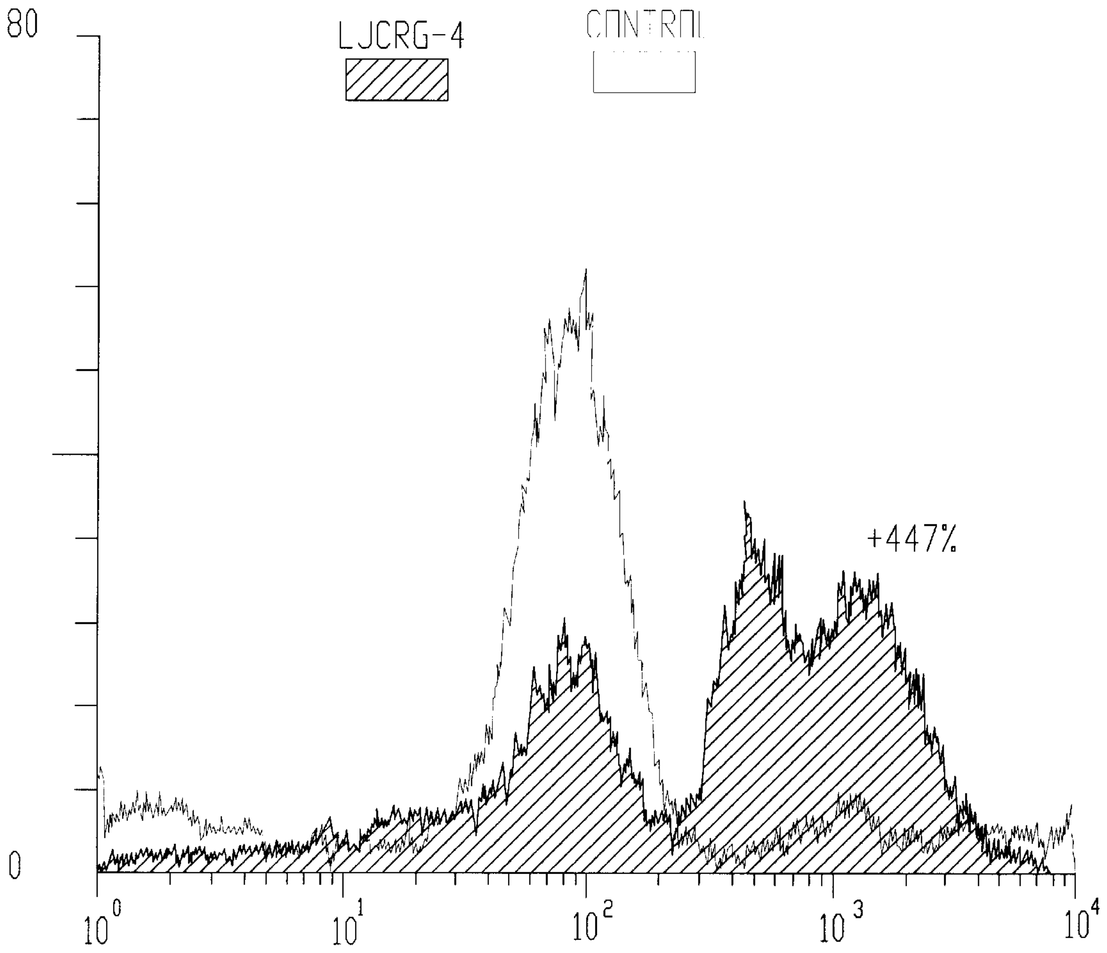
FIG. 4 depicts a plot of flow cytometer results for the LFA-1 based LJCRF-4 (Sequence ID No. 16) peptide, which functions to promote the specific antibody binding of anti-ICAM-1 mAb.

FIG. 4 (for sample LJCRF-4 at 4550 μM) is similar to FIGS. 2 and 3, but the +447% curve shift occurs in a positive direction, which indicates enhancement of the anti-ICAM antibody binding activity, not inhibition thereof.

Table 2, in part, provides a summary of the FACscan results for each of the peptides from which results were obtained. Most samples received multiple measurements, and the results varied appreciably for repeat tests within a given concentration. Accordingly, the Table 2 FACscan results include an average value for all of the median intensity peak values thus obtained; e.g., FIG. 4 depicts a +447% median peak enhancement for LJCRF-4 at 4550 μM, which was one enhancement value out of five such values that contributed to the overall average of +275±33 in Table 2. Standard error was calculated for each peptide as the standard deviation in the population of median peak intensity values divided by the square root of the number of intensity values.

The results of Table 2 indicate that several ICAM-1 or LFA-1 peptides having lengths from about 10–25 amino acid residues serve to regulate the binding of antibodies which are specific for the ligands of these peptides. For example, an ICAM-1 derived peptide such as SC-3-111 can bind with the ligand LFA-1 and inhibit the binding of a monoclonal antibody that is specific for LFA-1.

The LJCRF-2 peptide exhibited a capacity to block antibody binding at a 4550 μM concentration, but functioned to enhance such binding at a 2275 μM concentration.

EXAMPLE 3

Homotypic Adhesion Assay

An assay was performed to demonstrate that short-chain peptides can inhibit or enhance the intercellular adhesion between human T-cells by modulating the LFA/ICAM binding interaction between respective cells. As before, the T-cells were Molt3 cells prepared in RPMI 1640 growth medium according to Example 2. An approximate 7 ml aliquot of the growth medium was centrifuged (Jouan Model GT422 at 1400 rpm for 6.5 minutes), and the supernatant fluid was decanted. The pellet was resuspended in the supernatant fluid at titer of about $1\times10^6$ cells/ml, with the excess supernatant fluid being retained for future resuspension of the peptides.

A 228 nmol quantity of the LJCRF-1 (Sequence ID No. 6) peptide described in Table 1 was diluted with the supernatant fluid to a 500 μl final volume, and filtered in microcentrifuge filter tubes (0.22 micron filter; 3500 rpm for 6 minutes). Serial dilution of the filtered peptide with supernatant fluid was conducted to yield five 125 μl peptide solutions to give respective concentrations of about 115 μM, 230 μM, 460 μM, 910 μM, and 1.82 mM. At each concentration, a 125 μl portion of the cell suspension was pipetted into each 125 μl portion of the peptide solutions to yield combined samples having a 250 μl volume. The 250 μl samples were seeded into individual wells in a 48-well tissue culture grade plate (from Costar of Cambridge, Md.) and incubated at 37° C. for 30 minutes. Each sample received 5 μl of 2,5-methyl dihydroxy cinnamate ("MDHC") for a 10 μM final concentration, and was subsequently incubated for about 10 hours at 37° C. MDHC induces intercellular clumping of human T-cells (Tibbetts, Butler, and Benedict, submitted) by activating the LFA/ICAM binding interaction between respective cells.

Pictures were taken of five random fields per sample using an Olympus photomicroscope having a 0.8 mm field at 400×magnification, and a 3.2 mm field of view at 100× magnification. The amount of clumping observed was quantified by determining the mean number of clumps per field ± a standard error.

Figure 5:
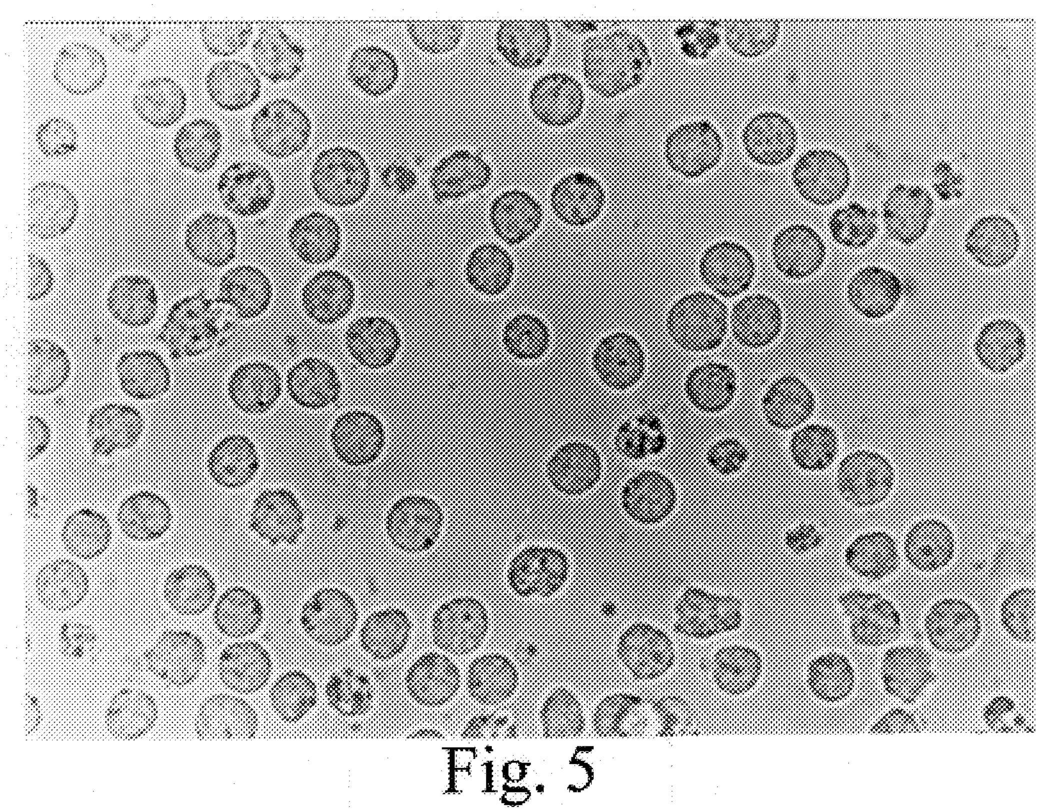
FIG. 5 is a photograph obtained from a control sample in a T-cell intercellular adhesion assay, wherein the cells demonstrated a natural lack of intercellular clumping.
Figure 6:
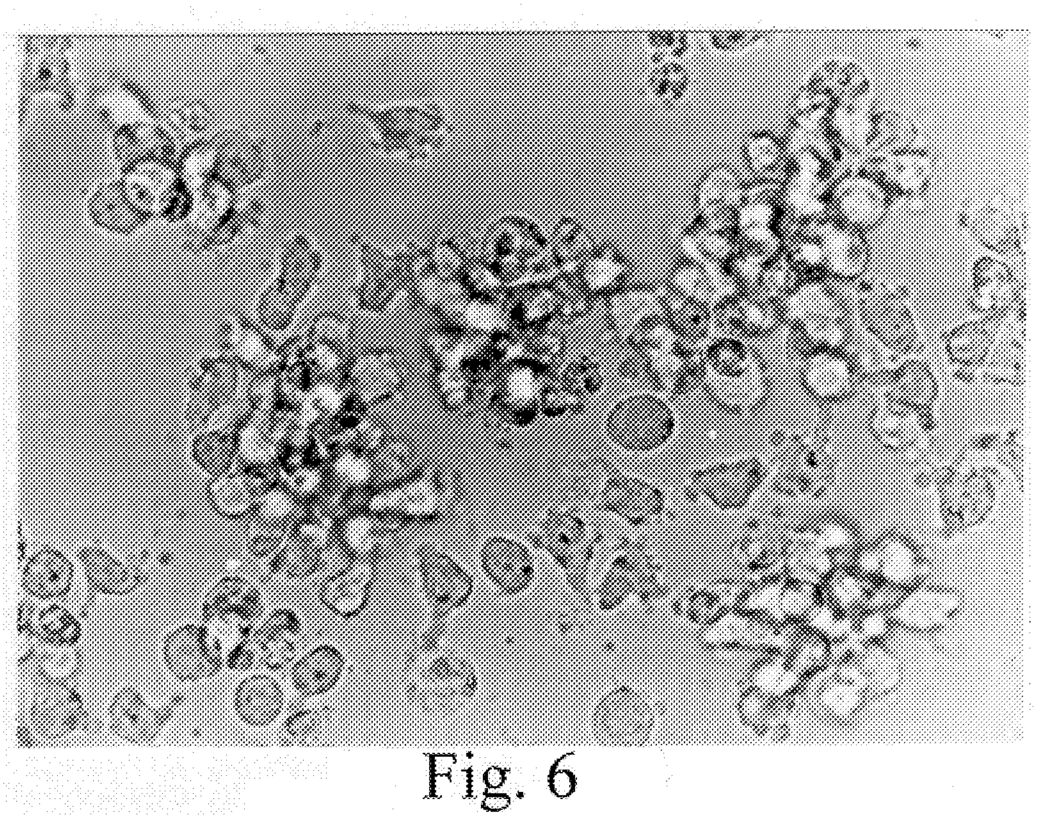
FIG. 6 is a photograph of a sample similar to that of FIG. 5, but in which a chemical additive has induced substantially complete intercellular clumping by way of the ICAM/LFA binding interaction.
Figure 7:
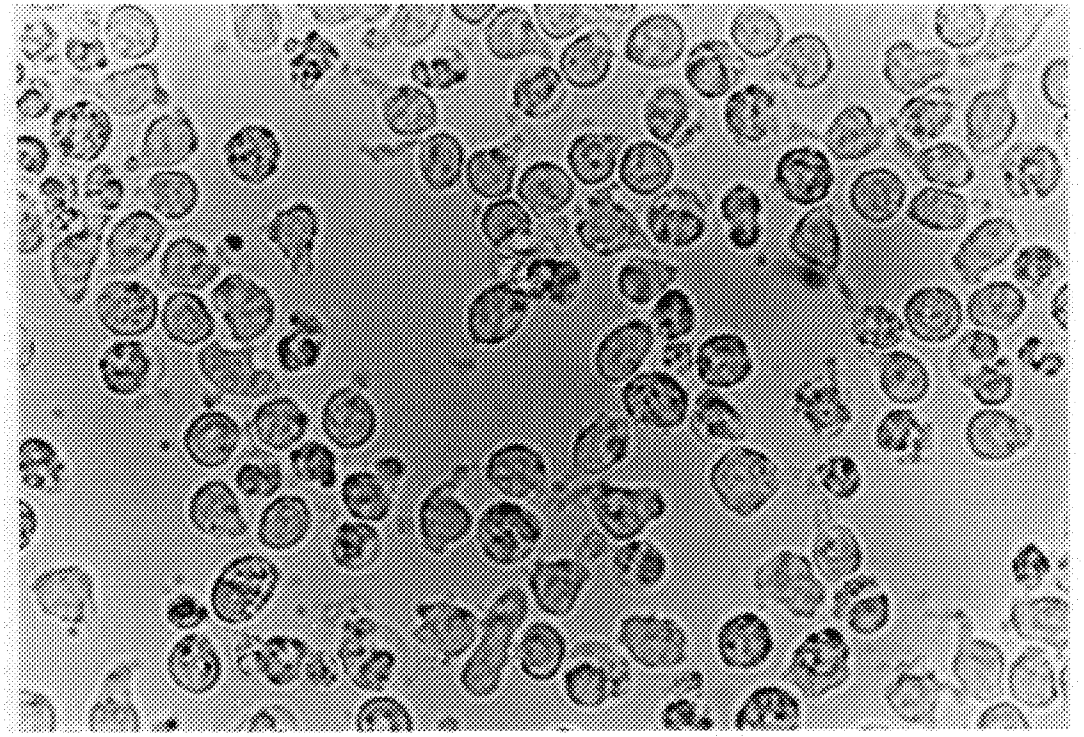
FIG. 7 is a photograph of a sample similar to that of FIG. 6, wherein a peptide of the invention has overcome the effect of the chemical additive to restore the sample to a state wherein substantially no intercellular clumping is observed.

The assay was repeatedly conducted for most of the short-chain peptides of Table 1, and these results are summarized below in Table 2. FIGS. 5, 6, and 7 replicate photographs taken from exemplary peptide assays. FIG. 5 is a photograph of the control sample having no peptides and no MDHC added, from which essentially no clumping of cells is observed. FIG. 6 depicts a photograph taken from a sample having MDHC added with no synthetic peptides, and demonstrates substantial clumping of cells. FIG. 7 depicts a photograph taken from the LJCRF-6 (Sequence ID No. 18) peptide assay at 910 μM, and demonstrates an almost total inhibition of MDHC induced clumping activity. Any sample having a score of "+++" or "++++" is considered to have a significant ability to modulate T-cell binding interaction. This is similar to results obtained by incubating similarly treated cells with antibody against either LFA or ICAM.

The homotypic adhesion assay assesses the actual ability of a candidate peptide to modulate the ability of T-cells to adhere with one another. At high concentrations, some of these peptides can function as blockers of intercellular adhesion, while having a capacity for functioning as binding enhancers at lower concentrations in growth medium; e.g., ICAM-derived LJCRF-2 at respective 910 and 460 μM concentrations, and LFA-derived derived LJCRF-4 at respective 230 and 460 μM concentrations.

EXAMPLE 4

Cell Metabolic Assay

After taking the photographs in Example 3 (and in some instances no photographs were taken), cell metabolic activity was assessed by an MTT assay. A 37.5 μl portion of MTT dye (purchased from SIGMA of St. Louis, Mo.), i.e., 3-[4, 5-dimethyl thiazole-2yl]-2, 5- diphenyl tetrazolium bromide; thiazolyl blue) was added to each well, and incubated with the cells at 37° C. for about six hours. After incubation, a 250 μl quantity of a MTT solubilization solution (of a type that may be purchased from either Fischer Scientific of St. Louis, Mo. or BCD Labs of Lawrence, Kans.) was added to each well, and incubated with the cells at room temperature overnight. In the morning, the spectrophotometric absorption of each plate was determined at 570 nm in a microplate ELISA reader manufactured by Cambridge Technologies of Water-town, Mass., in order to assess cell viability as an indicator of potential peptide toxicity.

The MTT assay is an index of the metabolic activity of the cells; any decrease in MTT absorbance reflects a decrease in metabolic activity., or indicates cell death. Some samples indicated a decrease in metabolic activity, especially at the higher concentrations, e.g., LJCRF-5 at 1820 μM. In other samples, cellular respiration was enhanced, e.g., MC-1-80 at 910 μM. The precise reasons for the observed decrease in metabolic activity are unknown, because this decrease may be caused by a number of factors. The possible causes of a decrease in metabolic activity include peptide toxicity, peptide toxicity in combination with MDHC, a simple reduction in the cellular metabolic rate.

Another possible cause of metabolic decline is that the peptides may cause the bound T-cells to die by apoptosis in a process similar to the thymic winnowing of immature T-cells. T-cells have very specific antigen receptors that serve to recognize foreign or non-self antigen complexes, and receive a first signal when they contact their particular antigen. After this initial contact, T-cells are activated to become cytotoxic T-cells by a second signal, i.e., the LFA/ICAM binding interaction. If the second signal never arrives, the cell is never activated, and is eventually induced to die by apoptosis. The peptides may induce this type of cellular death in these leukemic T-cells which are already activated by blocking the second signal (cytotoxic activation signal). Accordingly, the peptides may be utilized to induce specific immune tolerance by causing the deaths of T-cells that recognize antigens that are present at a specific time of treatment.

EXAMPLE 5

Use of Conformation Modulator Peptides

The LJCRF-2 and LJCRF-4 peptides ("modulator peptides") of Table 1 demonstrated a significant positive intensity shift in the corresponding FACS analysis of Table 2, i.e., a positive intensity shift indicating a capacity for enhancing the LFA/ICAM interaction between the T-cells and the antibody binding interaction. Following these results, a further assay was performed to ascertain the effect of sequentially combining short-chain blocker peptides with the short-chain modulator peptides of the invention. It was discovered that a combination of specific blocker and modulator peptides significantly improves the level of observed binding enhancement as quantified by a flow cytometric assay using fluorescinated peptides.

The antibody binding assay of Example 2 was twice repeated at a peptide concentration of 4550 μM, each time substituting a 455 nmol quantity of synthetic peptide selected from the group consisting of ICAM-based peptide SC-3-111 (Sequence ID No. 10) and LFA-based peptide LJCRF-4 (Sequence ID No. 16) in respective assays. Following incubation for 30 minutes at 37° C. after introduction of the first peptides, both incubated culture were supplemented by an additional quantity of FITC-labeled RB-1-88 (Sequence ID No. 19) peptide in a quantity sufficient to provide a 1.90 μM concentration in the cell/PBS solution.

Figure 8:
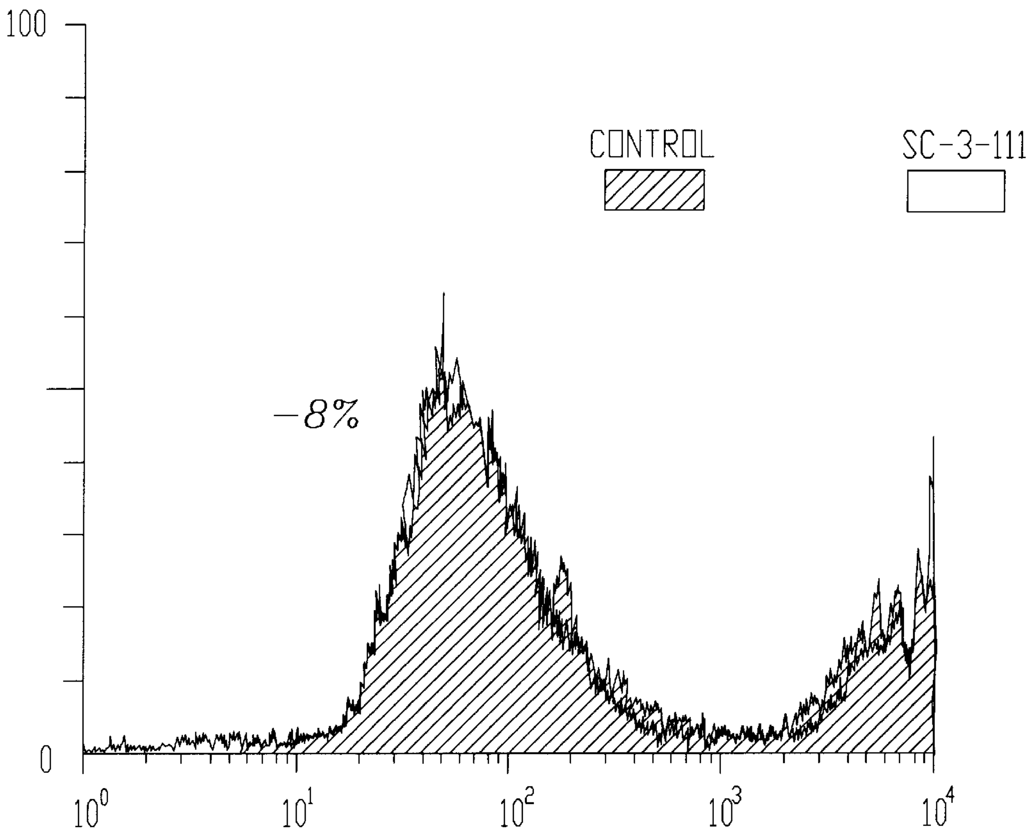
FIG. 8 depicts a plot of flow cytometer results that demonstrate substantially no T-cell binding enhancement of fluorecescein labeled LJCRF-6 (Sequence ID No. 18) peptide in the presence of SC-3-111 (Sequence ID No. 10) peptide.

Following addition of the RB-1-88 (Sequence ID No. 19) peptide, the mixture was incubated for 30 minutes at 4° C., washed three times with 500 μl PBS/BSA, resuspended in 500 μl PBS/BSA and immediately subjected to a flow cytometer analysis as before. Table 3 presents the results of this analysis, which are also depicted in FIGS. 8 (SC-3-111) and 9 (LJCRF-4).

Figure 9:
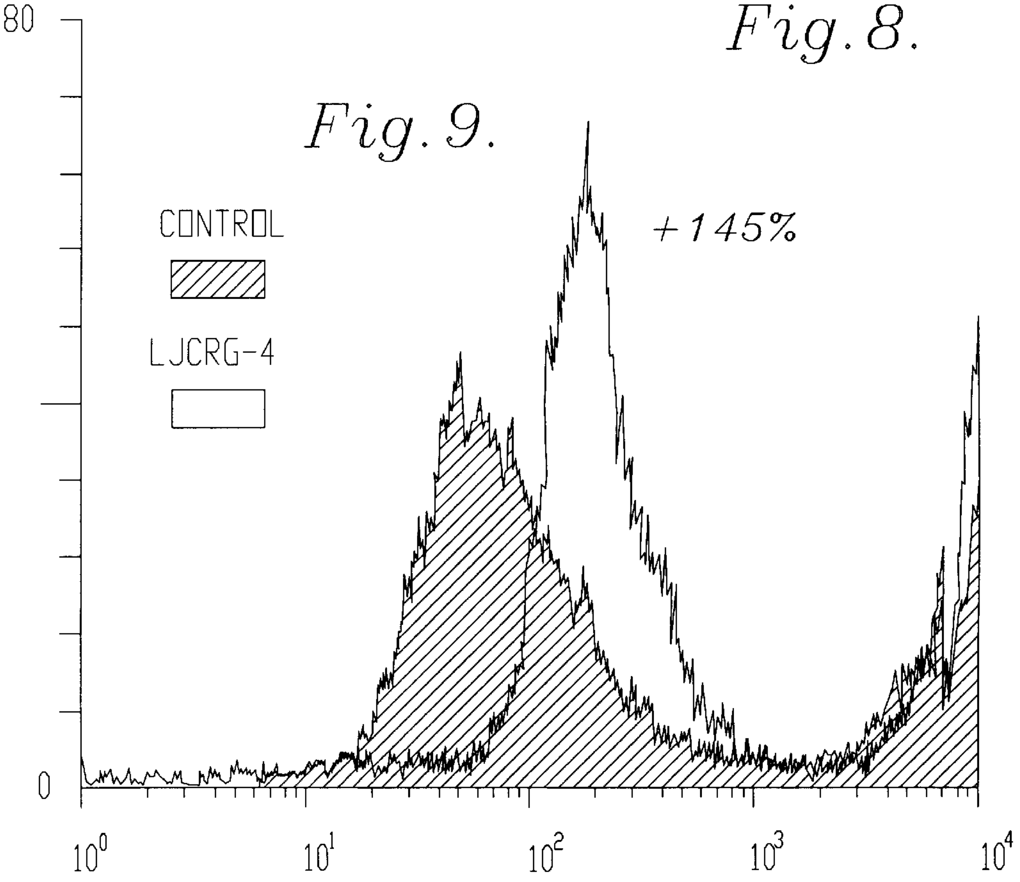
FIG. 9 depicts a plot of flow cytometer results that demonstrate significant T-cell binding enhancement of fluorecescein labeled LJCRF-6 (Sequence ID No. 18) peptide in the presence of LJCRF-4 (Sequence ID No. 16) peptide.

FIG. 9 depicts binding of RB-1-88 to T cells and the ability of LJCRF-4 to enhance the binding. Conversely, FIG. 8 demonstrates that the SC-3-111 peptide had no effect upon the ability of cell surface ICAM-1 to bind RB-1-88.

The results of Table 3 and FIG. 9 indicate that the LJCRF-4 peptide significantly enhanced the binding of RB-1-88 peptide to ICAM-1. Similar enhancement of the RB-1-88 peptide binding avidity was not observed in the presence of SC-3-111 peptide, inasmuch as the negative 8% blocking shift (FIG. 8) is probably not significant in terms of laboratory error.

The peptides that serve to promote interprotein binding capacities do so according to the steps of: (1) binding to the protein ligand at a first site, and (2) changing the conformation of the protein ligand to make a second site more available for binding with the corresponding monoclonal antibody or peptide counterpart to the protein ligand. By way of example, the LFA-derived LJCRF-4 modulator peptide inherently targets a corresponding ICAM protein. The resultant enhanced ICAM/LFA-type of reactive binding must result from a conformational change, but cannot result from phosphorylation-induced conformational changes because ICAM configuration is generally not influenced by cellular phosphorylation pathways.

TABLE 2

PEPTIDE RESULTS COMPARISON

| Peptides (Sequence ID No.) | | Antibody Binding (FACS Analysis) | | | | Homotypic Adhesion | | | | MTT | | |
|---|---|---|---|---|---|---|---|---|---|---|---|---|
| Peptide | Derivation | Tests Run | Conc. [μM] | Fluorescence[1] | mAb | Tests Run | Effect | Amount | Conc. [μM] | Test Runs | % Viability | Conc. [μM] |
| SC-3111 | ICAM-1 | 11 | 4550 | −29 ± 2 | CD11a | 3 | Block | +++ | 1820 | 3 | 69 | 1820 |
| (10) | | 6 | 2275 | −12 ± 4 | CD11a | 3 | Block | ++++ | 910 | 3 | 89 | 910 |
| | | | | | | 1 | Block | ++ | 460 | 2 | 95 | 460 |
| | | | | | | 1 | Block | + | 230 | 2 | 93 | 230 |
| | | | | | | | | | | 2 | 85 | |
| LJCRF-1 | ICAM-1 | 8 | 4550 | −29 ± 3 | CD11a | 2 | Block | +++ | 1820 | 2 | 66 | 1820 |
| (6) | | 6 | 2275 | −12 ± 2 | CD11a | 2 | Block | ++ | 910 | 2 | 92 | 910 |
| | | | | | | 1 | Block | +++ | 460 | 2 | 93 | 460 |
| | | | | | | | | | | 2 | 94 | |
| | | | | | | | | | | 2 | 112 | |
| SC-3-152 | ICAM-1 | 5 | 4550 | −43 ± 7 | CD11a | 2 | Block | ++++ | 1820 | 2 | 43 | 1820 |
| LJCRF-2 | | 4 | 2275 | +48 ± 8 | CD11a | 1 | Block | +++ | 910 | 2 | 38 | 910 |

TABLE 2-continued

PEPTIDE RESULTS COMPARISON

| Peptides | | Antibody Binding (FACS Analysis) | | | | Homotypic Adhesion | | | | MTT | | |
|---|---|---|---|---|---|---|---|---|---|---|---|---|
| (Sequence ID No.) | | Tests | Conc. | | | Tests | | | Conc. | Test | | Conc. |
| Peptide | Derivation | Run | [μM] | Fluorescence[1] | mAb | Run | Effect | Amount | [μM] | Runs | % Viability | [μM] |
| (11) | | | | | | 1 | Enhance | ++ | 460 | 2 | 38 | 460 |
| | | | | | | 1 | Enhance | +++ | 230 | 2 | 38 | 230 |
| | | | | | | | | | | 2 | 38 | |
| LJCRF-3 | ICAM-1 | 2 | 4550 | −13 ± 19 | CD11a | | | | | 2 | 38 | |
| (12) | | | | | | | | | | 2 | 38 | |
| | | | | | | | | | | 1 | 111 | |
| | | | | | | | | | | 1 | 109 | |
| | | | | | | | | | | 1 | 111 | |
| | | | | | | | | | | 1 | 97 | |
| MC-1-80 | ICAM-1 | | | | | | | | | 1 | 125 | |
| (9) | | | | | | | | | | 1 | 108 | |
| | | | | | | | | | | 1 | 89 | |
| | | | | | | | | | | 1 | 110 | |
| LJCRF-4 | LFA-1β | 1 | 6825 | +521 | CD54 | 1 | Block | +++ | 1820 | 2 | 11 | 1820 |
| (16) | | 5 | 4550 | +275 ± 33 | CDS4 | 1 | Block | ++++ | 910 | 3 | 60 | 910 |
| | | 2 | 2275 | +3 ± 1 | CD54 | 1 | Block | ++++ | 460 | 3 | 94 | 460 |
| | | | | | | 1 | Enhance | +++ | 230 | 3 | 101 | 230 |
| | | | | | | 1 | Enhance | +++ | 115 | 3 | 99 | 115 |
| SC-3-223 | LFA-1β | | | | | 2 | Block | ++++ | 1820 | 1 | 75 | 1820 |
| [Identical to | | | | | | 2 | Block | ++++ | 910 | 1 | 108 | 910 |
| LJCRF-4] | | | | | | 1 | Block | +++ | 460 | 1 | 112 | 460 |
| (16) | | | | | | 1 | Block | +++ | 230 | 1 | 109 | 230 |
| | | | | | | 1 | Block | ++ | 115 | 1 | 103 | 115 |
| LJCRF-5 | LFA-1α | 1 | 4550 | −17 | CD54 | 1 | Block | ++++ | 1820 | 3 | 20 | 1820 |
| (17) | | | | | | 1 | Block | ++++ | 910 | 3 | 52 | 910 |
| | | | | | | 1 | Block | ++ | 460 | 2 | 81 | 460 |
| | | | | | | 1 | Block | ++ | 230 | 2 | 84 | 230 |
| | | | | | | 1 | Block | ++ | 115 | 2 | 95 | 115 |
| LJCRF-6 | LFA-1α | 1 | 4550 | −4 | CD54 | 1 | Block | +++ | 1820 | | | 1820 |
| (18) | insert | | | | | | | | | 1 | 111 | |
| | | | | | | | | | | 1 | 109 | |
| | | | | | | | | | | 1 | 111 | |
| | | | | | | | | | | 1 | 97 | |

[1]% change from control of the medium fluorescence intensity

TABLE 3

SEQUENTIALLY COMBINED BLOCKER AND MODULATOR PEPTIDES

| Peptide | Sequence ID | FACS Analysis (RB-1-88 binding) |
|---|---|---|
| SC-3-111 | 10 | −8 |
| LJCRF-4 | 16 | +145 |

We claim:

1. A method for inhibiting the binding of a human ICAM-1 molecule to a human LFA-1 molecule comprising the steps of:

(a) providing a blocking peptide and a modulator peptide, wherein the blocking peptide has an binding affinity for the ICAM-1 molecule, and, when bound to the ICAM-1 molecule, inhibits the binding of the ICAM-1 molecule to the LFA-1 molecule; and a modulator peptide, wherein the modulator peptide, when bound to the ICAM-1 molecule, increases the binding affinity of the blocking peptide for the ICAM-1 molecule by inducing a conformational change in the ICAM-1 molecule, wherein the blocking peptide and the modulator peptide each comprise an amino acid sequence included in the amino acid sequence of the extracellular segment of the LFA-1 molecule and each have molecular weights of under 20 kilodaltons thereby making them nonimmunogenic in a human; and (b) contacting the blocking peptide and the modulator peptide with the ICAM-1 molecule, thereby inhibiting the binding of the ICAM-1 molecule to the LFA-1 molecule.

2. The method of claim 1, wherein the blocking peptide comprises an amino acid sequence selected from the group consisting of Sequence ID Nos. 16, 17, and 18.

3. The method of claim 1, wherein the modulator peptide comprises Sequence ID No. 16.

4. The method of claim 1, wherein the blocking peptide is prepared by a method comprising the steps of:

(a) identifying a first protein domain of the LFA-1 molecule wherein the first protein domain is capable of binding to the ICAM-1 molecule; and (b) synthesizing a blocking peptide comprising an amino acid sequence included in the first protein domain, wherein, in the antibody-binding assay of Example 2, the fluorescence intensity value calculated using a first sample lacking the blocking peptide is at least 10% higher than the fluorescence intensity value calculated using a second sample including the blocking peptide, wherein the modulator peptide is prepared by a method comprising the steps of:

(c) identifying a second protein domain of the LFA-1 molecule wherein the second protein domain is capable of binding to the ICAM-1 molecule; and (d) synthesizing the modulator peptide comprising an amino acid sequence included in the second protein domain, wherein, in the binding assay of Example 2, the fluorescence intensity value calculated using a first sample lacking the modulator peptide is at least 10% lower than the fluorescence intensity value calculated using a second sample including the modulator peptide.

5. The method of claim 4, wherein the blocking peptide comprises an amino acid sequence selected from the group consisting of Sequence ID Nos. 16, 17, and 18.

6. The method of claim 4, wherein the modulator peptide comprises Sequence ID No.16.

7. A method for inhibiting the binding of a human LFA-1 molecule to a human ICAM-1 molecule comprising the steps of:

(a) providing a blocking peptide and a modulator peptide, wherein the blocking peptide has an initial binding affinity for the LFA-1 molecule, and, when bound to the LFA-1 molecule, inhibits the binding of the LFA-1 molecule to the ICAM-1 molecule; and a modulator peptide, wherein the modulator peptide, when bound to the LFA-1 molecule, increases the binding affinity of the blocking peptide for the LFA-1 molecule by inducing a conformational change in the LFA-1 molecule, wherein the blocking peptide and the modulator peptide each comprise an amino acid sequence included in the amino acid sequence of the extracellular segment of the ICAM-1 molecule and each have molecular weights of under 20 kilodaltons thereby making them nonimmunogenic in a human; and (b) contacting the blocking peptide and the modulator peptide with the LFA-1 molecule, thereby inhibiting the binding of the LFA-1 molecule to the ICAM-1 molecule.

8. The method of claim 7, wherein the blocking peptide comprises an amino acid sequence selected from the group consisting of Sequence ID Nos. 6, 10, 11, and 12.

9. The method of claim 7, wherein the modulator peptide comprises Sequence ID No. 11.

10. The method of claim 7, wherein the blocking peptide is prepared by a method comprising the steps of:

(a) identifying a first protein domain of the ICAM-1 molecule wherein the first protein domain is capable of binding to the LFA-1 molecule; and (b) synthesizing a blocking peptide comprising an amino acid sequence included in the first protein domain, wherein, in the antibody-binding assay of Example 2, the fluorescence intensity value calculated using a first sample lacking the blocking peptide is at least 10% higher than the fluorescence intensity value calculated using a second sample including the blocking peptide, wherein the modulator peptide is prepared by a method comprising the steps of:

(c) identifying a second protein domain of the ICAM-1 molecule wherein the second protein domain is capable of binding to the LFA-1 molecule; and (d) synthesizing the modulator peptide comprising an amino acid sequence included in the second protein domain, wherein, in the binding assay of Example 2, the fluorescence intensity value calculated using a first sample lacking the modulator peptide is at least 10% lower than the fluorescence intensity value calculated using a second sample including the modulator peptide.

11. The method of claim 10, wherein the blocking peptide comprises an amino acid sequence selected from the group consisting of Sequence ID Nos. 6,10, 11, and 12.

12. The method of claim 10, wherein the modulator peptide comprises Sequence ID No.11.

13. Method for inhibiting the interaction between ICAM-1 and LFA-1, said method comprising the steps of:

(a) providing a blocking peptide comprising a first amino acid sequence of the extracellular segment of one of the human LFA-1 or human ICAM-1 molecule and having a molecular weight of under 20 kilodaltons, said blocking peptide being capable of binding to a target molecule, which is the other of said human LFA-1 or human ICAM-1 molecule, for inhibiting said LFA-1/ICAM-1 interaction, said blocking peptide characterized by the property of having a fluorescence intensity value calculated using a first sample lacking said blocking peptide at least 10% higher than the fluorescence intensity value calculated using a second sample including said blocking peptide, in the antibody-binding assay conducted as described in Example 2;

(b) providing a modulator peptide comprising a second amino acid sequence of the extracellular segment of said one of the human LFA-1 or human ICAM-1 molecule which is different than said first sequence, and having molecular weight of under 20 kilodaltons, said modulator peptide being capable of binding to said target molecule for increasing the affinity of said blocking peptide for said target molecule, said modulator peptide characterized by the property of having a fluorescence intensity value calculated using a first sample lacking the modulator peptide of at least 10% lower than the fluorescence intensity value calculated using a second sample including the modulator peptide in the assay of Example 2; and, (c) contacting said blocking peptide and said modulator peptide with said target molecule, thereby inhibiting said ICAM-1/LFA-1 interaction.

14. The method of claim 13, said one of said human LFA-1 or human ICAM-1 molecule being LFA-1, and said target molecule being ICAM-1.

15. The method of claim 13, said one of said human LFA-1 or human ICAM-1 molecule being ICAM-1, and said target molecule being LFA-1.

16. The method of claim 13, said blocking peptide being selected from the group consisting of Sequence ID Nos. 6. 17, and 18.

17. The method of claim 13, said modulator peptide being selected from the group consisting of Sequence ID Nos. 11 and 16.

18. A method of enhancing the interaction between ICAM-1 and LFA-1 comprising:

(a) providing a modulator peptide comprising an amino acid sequence of the extracellular segment of one of the human LFA-1 or human ICAM-1 molecule, and having a molecular weight of under 20 kilodaltons, said modulator peptide characterized by the property of having a fluorescence intensity value calculated using a first sample lacking said modulator peptide of at least 10% lower than the fluorescence intensity value calculated using a second sample including the modulator peptide in the assay of Example 2; and, (b) contacting said modulator peptide with the other of said human LFA-1 or human ICAM-1 molecule, thereby enhancing said ICAM-1/LFA-1 interaction.

* * * * *

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
( A ) LENGTH: 769 amino acids
( B ) TYPE: amino acid -continued ( D ) TOPOLOGY: both ( i i ) MOLECULE TYPE: protein ( i i i ) HYPOTHETICAL: NO ( v i ) ORIGINAL SOURCE:
( A ) ORGANISM: Homo sapiens
( F ) TISSUE TYPE: Tonsil ( i x ) FEATURE:
( A ) NAME/KEY: Region
( B ) LOCATION: 1..22
( D ) OTHER INFORMATION: /labels=signal
/ note= "signal sequence"

( i x ) FEATURE:
( A ) NAME/KEY: Region
( B ) LOCATION: 449..496
( D ) OTHER INFORMATION: /label=repeat
/ note= "cysteine rich repeat"

( i x ) FEATURE:
( A ) NAME/KEY: Region
( B ) LOCATION: 497..540
( D ) OTHER INFORMATION: /label=repeat
/ note= "cysteine rich repeat"

( i x ) FEATURE:
( A ) NAME/KEY: Region
( B ) LOCATION: 541..581
( D ) OTHER INFORMATION: /label=repeat
/ note= "cysteine rich repeat"

( i x ) FEATURE:
( A ) NAME/KEY: Region
( B ) LOCATION: 582..617
( D ) OTHER INFORMATION: /label=repeat
/ note= "cysteine rich repeat"

( i x ) FEATURE:
( A ) NAME/KEY: Domain
( B ) LOCATION: 701..723
( D ) OTHER INFORMATION: /label=trans
/ note= "transmembrane domain"

( i x ) FEATURE:
( A ) NAME/KEY: Domain
( B ) LOCATION: 724..769
( D ) OTHER INFORMATION: /label=cyto
/ note= "cytoplasmic domain"

( x ) PUBLICATION INFORMATION:
( A ) AUTHORS: Pigott,
Power,
( B ) TITLE: LFA-1 Amino acid sequence (B2) (from human
tonsil)
( C ) JOURNAL: The Adhesion Molecule Facts Book
( F ) PAGES: 96-96
( G ) DATE: 1993
( K ) RELEVANT RESIDUES IN SEQ ID NO:1: FROM 1 TO 769

( x i ) SEQUENCE DESCRIPTION: SEQ ID NO:1:

Met Leu Gly Leu Arg Pro Pro Leu Leu Ala Leu Val Gly Leu Leu Ser
1 5 10 15

Leu Gly Cys Val Leu Ser Gln Glu Cys Thr Lys Phe Lys Val Ser Ser
20 25 30

Cys Arg Glu Cys Ile Glu Ser Gly Pro Gly Cys Thr Trp Cys Gln Lys
35 40 45

Leu Asn Phe Thr Gly Pro Gly Asp Pro Asp Ser Ile Arg Cys Asp Thr
50 55 60

Arg Pro Gln Leu Leu Met Arg Gly Cys Ala Ala Asp Asp Ile Met Asp
65 70 75 80

Pro Thr Ser Leu Ala Glu Thr Gln Glu Asp His Asn Gly Gly Gln Lys

-continued

```
                    85                      90                      95
Gln Leu Ser Pro Gln Lys Val Thr Leu Tyr Leu Arg Pro Gly Gln Ala
            100                     105                     110
Ala Ala Phe Asn Val Thr Phe Arg Arg Ala Lys Gly Tyr Pro Ile Asp
        115                     120                     125
Leu Tyr Tyr Leu Met Asp Leu Ser Tyr Ser Met Leu Asp Asp Leu Arg
    130                     135                     140
Asn Val Lys Lys Leu Gly Gly Asp Leu Leu Arg Ala Leu Asn Glu Ile
145                     150                     155                     160
Thr Glu Ser Gly Arg Ile Gly Phe Gly Ser Phe Val Asp Lys Thr Val
                165                     170                     175
Leu Pro Phe Val Asn Thr His Pro Asp Lys Leu Arg Asn Pro Cys Pro
            180                     185                     190
Asn Lys Glu Lys Glu Cys Gln Pro Pro Phe Ala Phe Arg His Val Leu
        195                     200                     205
Lys Leu Thr Asn Asn Ser Asn Gln Phe Gln Thr Glu Val Gly Lys Gln
    210                     215                     220
Leu Ile Ser Gly Asn Leu Asp Ala Pro Glu Gly Gly Leu Asp Ala Met
225                     230                     235                     240
Met Gln Val Ala Ala Cys Pro Glu Glu Ile Gly Trp Arg Asn Val Thr
                245                     250                     255
Arg Leu Leu Val Phe Ala Thr Asp Asp Gly Phe His Phe Ala Gly Asp
            260                     265                     270
Gly Lys Leu Gly Ala Ile Leu Thr Pro Asn Asp Gly Arg Cys His Leu
        275                     280                     285
Glu Asp Asn Leu Tyr Lys Arg Ser Asn Glu Phe Asp Tyr Pro Ser Val
    290                     295                     300
Gly Gln Leu Ala His Lys Leu Ala Glu Asn Asn Ile Gln Pro Ile Phe
305                     310                     315                     320
Ala Val Thr Ser Arg Met Val Lys Thr Tyr Glu Lys Leu Thr Glu Ile
                325                     330                     335
Ile Pro Lys Ser Ala Val Gly Glu Leu Ser Glu Asp Ser Ser Asn Val
            340                     345                     350
Val His Leu Ile Lys Asn Ala Tyr Asn Lys Leu Ser Ser Arg Val Phe
        355                     360                     365
Leu Asp His Asn Ala Leu Pro Asp Thr Leu Lys Val Thr Tyr Asp Ser
    370                     375                     380
Phe Cys Ser Asn Gly Val Thr His Arg Asn Gln Pro Arg Gly Asp Cys
385                     390                     395                     400
Asp Gly Val Gln Ile Asn Val Pro Ile Thr Phe Gln Val Lys Val Thr
                405                     410                     415
Ala Thr Glu Cys Ile Gln Glu Gln Ser Phe Val Ile Arg Ala Leu Gly
            420                     425                     430
Phe Thr Asp Ile Val Thr Val Gln Val Leu Pro Gln Cys Glu Cys Arg
        435                     440                     445
Cys Arg Asp Gln Ser Arg Asp Arg Ser Leu Cys His Gly Lys Gly Phe
    450                     455                     460
Leu Glu Cys Gly Ile Cys Arg Cys Asp Thr Gly Tyr Ile Gly Lys Asn
465                     470                     475                     480
Cys Glu Cys Gln Thr Gln Gly Arg Ser Ser Gln Glu Leu Glu Gly Ser
                485                     490                     495
Cys Arg Lys Asp Asn Asn Ser Ile Ile Cys Ser Gly Leu Gly Asp Cys
            500                     505                     510
```

-continued

Val Cys Gly Gln Cys Leu Cys His Thr Ser Asp Val Pro Gly Lys Leu
515 520 525

Ile Tyr Gly Gln Tyr Cys Glu Cys Asp Thr Ile Asn Cys Glu Arg Tyr
530 535 540

Asn Gly Gln Val Cys Gly Gly Pro Gly Arg Gly Leu Cys Phe Cys Gly
545 550 555 560

Lys Cys Arg Cys His Pro Gly Phe Glu Gly Ser Ala Cys Gln Cys Glu
565 570 575

Arg Thr Thr Glu Gly Cys Leu Asn Pro Arg Arg Val Glu Cys Ser Gly
580 585 590

Arg Gly Arg Cys Arg Cys Asn Val Cys Glu Cys His Ser Gly Tyr Gln
595 600 605

Leu Pro Leu Cys Gln Glu Cys Pro Gly Cys Pro Ser Pro Cys Gly Lys
610 615 620

Tyr Ile Ser Cys Ala Glu Cys Leu Lys Phe Glu Lys Gly Pro Phe Gly
625 630 635 640

Lys Asn Cys Ser Ala Ala Cys Pro Gly Leu Gln Leu Ser Asn Asn Pro
645 650 655

Val Lys Gly Arg Thr Cys Lys Glu Arg Asp Ser Glu Gly Cys Trp Val
660 665 670

Ala Tyr Thr Leu Glu Gln Gln Asp Gly Met Asp Arg Tyr Leu Ile Tyr
675 680 685

Val Asp Glu Ser Arg Glu Cys Val Ala Gly Pro Asn Ile Ala Ala Ile
690 695 700

Val Gly Gly Thr Val Ala Gly Ile Val Leu Ile Gly Ile Leu Leu Leu
705 710 715 720

Val Ile Trp Lys Ala Leu Ile His Leu Ser Asp Leu Arg Glu Tyr Arg
725 730 735

Arg Phe Glu Lys Glu Lys Leu Lys Ser Gln Trp Asn Asn Asp Asn Pro
740 745 750

Leu Phe Lys Ser Ala Thr Thr Thr Val Met Asn Pro Lys Phe Ala Glu
755 760 765

Ser ( 2 ) INFORMATION FOR SEQ ID NO:2:

( i ) SEQUENCE CHARACTERISTICS:
( A ) LENGTH: 1170 amino acids
( B ) TYPE: amino acid
( D ) TOPOLOGY: linear ( i i ) MOLECULE TYPE: protein ( i i i ) HYPOTHETICAL: NO ( v i ) ORIGINAL SOURCE:
( A ) ORGANISM: Homo sapiens
( G ) CELL TYPE: T-cell
( H ) CELL LINE: HL-60

( i x ) FEATURE:
( A ) NAME/KEY: Region
( B ) LOCATION: 1..25
( D ) OTHER INFORMATION: /label=signal
/ note= "Signal sequence"

( i x ) FEATURE:
( A ) NAME/KEY: Region
( B ) LOCATION: 32..79
( D ) OTHER INFORMATION: /label=Repeat
/ note= "Repeat I"

( i x ) FEATURE:

-continued ( A ) NAME/KEY: Region
( B ) LOCATION: 82..132
( D ) OTHER INFORMATION: /label=Repeat
/ note= "Repeat II"

( i x ) FEATURE:
( A ) NAME/KEY: Region
( B ) LOCATION: 339..391
( D ) OTHER INFORMATION: /label=Repeat
/ note= "Repeat III"

( i x ) FEATURE:
( A ) NAME/KEY: Region
( B ) LOCATION: 392..446
( D ) OTHER INFORMATION: /label=Repeat
/ note= "Repeat IV"

( i x ) FEATURE:
( A ) NAME/KEY: Region
( B ) LOCATION: 447..508
( D ) OTHER INFORMATION: /label=Repeat
/ note= "Repeat V"

( i x ) FEATURE:
( A ) NAME/KEY: Region
( B ) LOCATION: 509..567
( D ) OTHER INFORMATION: /label=Repeat
/ note= "Repeat VI"

( i x ) FEATURE:
( A ) NAME/KEY: Region
( B ) LOCATION: 568..629
( D ) OTHER INFORMATION: /label=Repeat
/ note= "Repeat VII"

( i x ) FEATURE:
( A ) NAME/KEY: Domain
( B ) LOCATION: 170..349
( D ) OTHER INFORMATION: /label=IDomain
/ note= "I-Domain"

( i x ) FEATURE:
( A ) NAME/KEY: Domain
( B ) LOCATION: 1089..1112
( D ) OTHER INFORMATION: /label=Trans
/ note= "Transmembrane Domain"

( i x ) FEATURE:
( A ) NAME/KEY: Domain
( B ) LOCATION: 1113..1170
( D ) OTHER INFORMATION: /label=Cyto
/ note= "Cytoplasmic domain"

( x ) PUBLICATION INFORMATION:
( A ) AUTHORS: Pigott,
Power,
( B ) TITLE: LFA-1 Amino acid sequence (alphaL) (from
PMA- stimulated HL-60 cells)
( C ) JOURNAL: The Adhesion Molecule Facts Book
( F ) PAGES: 94-95
( G ) DATE: 1993
( K ) RELEVANT RESIDUES IN SEQ ID NO:2: FROM 1 TO 1170

( x i ) SEQUENCE DESCRIPTION: SEQ ID NO:2:

Met Lys Asp Ser Cys Ile Thr Val Met Ala Met Ala Leu Leu Ser Gly
1 5 10 15

Phe Phe Phe Phe Ala Pro Ala Ser Ser Tyr Asn Leu Asp Val Arg Gly
20 25 30

Ala Arg Ser Phe Ser Pro Pro Arg Ala Gly Arg His Phe Gly Tyr Arg
35 40 45

Val Leu Gln Val Gly Asn Gly Val Ile Val Gly Ala Pro Gly Glu Gly
50 55 60

Asn Ser Thr Gly Ser Leu Tyr Gln Cys Gln Ser Gly Thr Gly His Cys
65 70 75 80

-continued

| | | | | | | | | | | | | | | | |
|---|---|---|---|---|---|---|---|---|---|---|---|---|---|---|---|
| Leu | Pro | Val | Thr | Leu | Arg | Gly | Ser | Asn | Tyr | Thr | Ser | Lys | Tyr | Leu | Gly |
| | | | | 85 | | | | | 90 | | | | | 95 | |
| Met | Thr | Leu | Ala | Thr | Asp | Pro | Thr | Asp | Gly | Ser | Ile | Leu | Ala | Cys | Asp |
| | | | 100 | | | | | 105 | | | | | 110 | | |
| Pro | Gly | Leu | Ser | Arg | Thr | Cys | Asp | Gln | Asn | Thr | Tyr | Leu | Ser | Gly | Leu |
| | | 115 | | | | | 120 | | | | | 125 | | | |
| Cys | Tyr | Leu | Phe | Arg | Gln | Asn | Leu | Gln | Gly | Pro | Met | Leu | Gln | Gly | Arg |
| | 130 | | | | | 135 | | | | | 140 | | | | |
| Pro | Gly | Phe | Gln | Glu | Cys | Ile | Lys | Gly | Asn | Val | Asp | Leu | Val | Phe | Leu |
| 145 | | | | | 150 | | | | | 155 | | | | | 160 |
| Phe | Asp | Gly | Ser | Met | Ser | Leu | Gln | Pro | Asp | Glu | Phe | Gln | Lys | Ile | Leu |
| | | | | 165 | | | | | 170 | | | | | 175 | |
| Asp | Phe | Met | Lys | Asp | Val | Met | Lys | Lys | Leu | Ser | Asn | Thr | Ser | Tyr | Gln |
| | | | 180 | | | | | 185 | | | | | 190 | | |
| Phe | Ala | Ala | Val | Gln | Phe | Ser | Thr | Ser | Tyr | Lys | Thr | Glu | Phe | Asp | Phe |
| | | 195 | | | | | 200 | | | | | 205 | | | |
| Ser | Asp | Tyr | Val | Lys | Trp | Lys | Asp | Pro | Asp | Ala | Leu | Leu | Lys | His | Val |
| | 210 | | | | | 215 | | | | | 220 | | | | |
| Lys | His | Met | Leu | Leu | Leu | Thr | Asn | Thr | Phe | Gly | Ala | Ile | Asn | Tyr | Val |
| 225 | | | | | 230 | | | | | 235 | | | | | 240 |
| Ala | Thr | Glu | Val | Phe | Arg | Glu | Glu | Leu | Gly | Ala | Arg | Pro | Asp | Ala | Thr |
| | | | | 245 | | | | | 250 | | | | | 255 | |
| Lys | Val | Leu | Ile | Ile | Ile | Thr | Asp | Gly | Glu | Ala | Thr | Asp | Ser | Gly | Asn |
| | | | 260 | | | | | 265 | | | | | 270 | | |
| Ile | Asp | Ala | Ala | Lys | Asp | Ile | Ile | Arg | Tyr | Ile | Ile | Gly | Ile | Gly | Lys |
| | | 275 | | | | | 280 | | | | | 285 | | | |
| His | Phe | Gln | Thr | Lys | Glu | Ser | Gln | Glu | Thr | Leu | His | Lys | Phe | Ala | Ser |
| | 290 | | | | | 295 | | | | | 300 | | | | |
| Lys | Pro | Ala | Ser | Glu | Phe | Val | Lys | Ile | Leu | Asp | Thr | Phe | Glu | Lys | Leu |
| 305 | | | | | 310 | | | | | 315 | | | | | 320 |
| Lys | Asp | Leu | Phe | Thr | Glu | Leu | Gln | Lys | Lys | Ile | Tyr | Val | Ile | Glu | Gly |
| | | | | 325 | | | | | 330 | | | | | 335 | |
| Thr | Ser | Lys | Gln | Asp | Leu | Thr | Ser | Phe | Asn | Met | Glu | Leu | Ser | Ser | Ser |
| | | | 340 | | | | | 345 | | | | | 350 | | |
| Gly | Ile | Ser | Ala | Asp | Leu | Ser | Arg | Gly | His | Ala | Val | Val | Gly | Ala | Val |
| | | 355 | | | | | 360 | | | | | 365 | | | |
| Gly | Ala | Lys | Asp | Trp | Ala | Gly | Gly | Phe | Leu | Asp | Leu | Lys | Ala | Asp | Leu |
| | 370 | | | | | 375 | | | | | 380 | | | | |
| Gln | Asp | Asp | Thr | Phe | Ile | Gly | Asn | Glu | Pro | Leu | Thr | Pro | Glu | Val | Arg |
| 385 | | | | | 390 | | | | | 395 | | | | | 400 |
| Ala | Gly | Tyr | Leu | Gly | Tyr | Thr | Val | Thr | Trp | Leu | Pro | Ser | Arg | Gln | Lys |
| | | | | 405 | | | | | 410 | | | | | 415 | |
| Thr | Ser | Leu | Leu | Ala | Ser | Gly | Ala | Pro | Arg | Tyr | Gln | His | Met | Gly | Arg |
| | | | 420 | | | | | 425 | | | | | 430 | | |
| Val | Leu | Leu | Phe | Gln | Glu | Pro | Gln | Gly | Gly | Gly | His | Trp | Ser | Gln | Val |
| | | 435 | | | | | 440 | | | | | 445 | | | |
| Gln | Thr | Ile | His | Gly | Thr | Gln | Ile | Gly | Ser | Tyr | Phe | Gly | Gly | Glu | Leu |
| | 450 | | | | | 455 | | | | | 460 | | | | |
| Cys | Gly | Val | Asp | Val | Asp | Gln | Asp | Gly | Glu | Thr | Glu | Leu | Leu | Leu | Ile |
| 465 | | | | | 470 | | | | | 475 | | | | | 480 |
| Gly | Ala | Pro | Leu | Phe | Tyr | Gly | Glu | Gln | Arg | Gly | Gly | Arg | Val | Phe | Ile |
| | | | | 485 | | | | | 490 | | | | | 495 | |
| Tyr | Gln | Arg | Arg | Gln | Leu | Gly | Phe | Glu | Glu | Val | Ser | Glu | Leu | Gln | Gly |
| | | | 500 | | | | | 505 | | | | | 510 | | |

-continued

Asp Pro Gly Tyr Pro Leu Gly Arg Phe Gly Glu Ala Ile Thr Ala Leu
515 520 525

Thr Asp Ile Asn Gly Asp Gly Leu Val Asp Val Ala Val Gly Ala Pro
530 535 540

Leu Glu Glu Gln Gly Ala Val Tyr Ile Phe Asn Gly Arg His Gly Gly
545 550 555 560

Leu Ser Pro Gln Pro Ser Gln Arg Ile Glu Gly Thr Gln Val Leu Ser
565 570 575

Gly Ile Gln Trp Phe Gly Arg Ser Ile His Gly Val Lys Asp Leu Glu
580 585 590

Gly Asp Gly Leu Ala Asp Val Ala Val Gly Ala Glu Ser Gln Met Ile
595 600 605

Val Leu Ser Ser Arg Pro Val Val Asp Met Val Thr Leu Met Ser Phe
610 615 620

Ser Pro Ala Glu Ile Pro Val His Glu Val Glu Cys Ser Tyr Ser Thr
625 630 635 640

Ser Asn Lys Met Lys Glu Gly Val Asn Ile Thr Ile Cys Phe Gln Ile
645 650 655

Lys Ser Leu Tyr Pro Gln Phe Gln Gly Arg Leu Val Ala Asn Leu Thr
660 665 670

Tyr Thr Leu Gln Leu Asp Gly His Arg Thr Arg Arg Arg Gly Leu Phe
675 680 685

Pro Gly Gly Arg His Glu Leu Arg Arg Asn Ile Ala Val Thr Thr Ser
690 695 700

Met Ser Cys Thr Asp Phe Ser Phe His Phe Pro Val Cys Val Gln Asp
705 710 715 720

Leu Ile Ser Pro Ile Asn Val Ser Leu Asn Phe Ser Leu Trp Glu Glu
725 730 735

Glu Gly Thr Pro Arg Asp Gln Arg Ala Gln Gly Lys Asp Ile Pro Pro
740 745 750

Ile Leu Arg Pro Ser Leu His Ser Glu Thr Trp Glu Ile Pro Phe Glu
755 760 765

Lys Asn Cys Gly Glu Asp Lys Lys Cys Glu Ala Asn Leu Arg Val Ser
770 775 780

Phe Ser Pro Ala Arg Ser Arg Ala Leu Arg Leu Thr Ala Phe Ala Ser
785 790 795 800

Leu Ser Val Glu Leu Ser Leu Ser Asn Leu Glu Glu Asp Ala Tyr Trp
805 810 815

Val Gln Leu Asp Leu His Phe Pro Pro Gly Leu Ser Phe Arg Lys Val
820 825 830

Glu Met Leu Lys Pro His Ser Gln Ile Pro Val Ser Cys Glu Glu Leu
835 840 845

Pro Glu Glu Ser Arg Leu Leu Ser Arg Ala Leu Ser Cys Asn Val Ser
850 855 860

Ser Pro Ile Phe Lys Ala Gly His Ser Val Ala Leu Gln Met Met Phe
865 870 875 880

Asn Thr Leu Val Asn Ser Ser Trp Gly Asp Ser Val Glu Leu His Ala
885 890 895

Asn Val Thr Cys Asn Asn Glu Asp Ser Asp Leu Leu Glu Asp Asn Ser
900 905 910

Ala Thr Thr Ile Ile Pro Ile Leu Tyr Pro Ile Asn Ile Leu Ile Gln
915 920 925

Asp Gln Glu Asp Ser Thr Leu Tyr Val Ser Phe Thr Pro Lys Gly Pro

-continued 930 935 940

Lys Ile His Gln Val Lys His Met Tyr Gln Val Arg Ile Gln Pro Ser
945 950 955 960

Ile His Asp His Asn Ile Pro Thr Leu Glu Ala Val Val Gly Val Pro
965 970 975

Gln Pro Pro Ser Glu Gly Pro Ile Thr His Gln Trp Ser Val Gln Met
980 985 990

Glu Pro Pro Val Pro Cys His Tyr Glu Asp Leu Glu Arg Leu Pro Asp
995 1000 1005

Ala Ala Glu Pro Cys Leu Pro Gly Ala Leu Phe Arg Cys Pro Val Val
1010 1015 1020

Phe Arg Gln Glu Ile Leu Val Gln Val Ile Gly Thr Leu Glu Leu Val
1025 1030 1035 1040

Gly Glu Ile Glu Ala Ser Ser Met Phe Ser Leu Cys Ser Ser Leu Ser
1045 1050 1055

Ile Ser Phe Asn Ser Ser Lys His Phe His Leu Tyr Gly Ser Asn Ala
1060 1065 1070

Ser Leu Ala Gln Val Val Met Lys Val Asp Val Val Tyr Glu Lys Gln
1075 1080 1085

Met Leu Tyr Leu Tyr Val Leu Ser Gly Ile Gly Gly Leu Leu Leu Leu
1090 1095 1100

Leu Leu Ile Phe Ile Val Leu Tyr Lys Val Gly Phe Phe Lys Arg Asn
1105 1110 1115 1120

Leu Lys Glu Lys Met Glu Ala Gly Arg Gly Val Pro Asn Gly Ile Pro
1125 1130 1135

Ala Glu Asp Ser Glu Gln Leu Ala Ser Gly Gln Glu Ala Gly Asp Pro
1140 1145 1150

Gly Cys Leu Lys Pro Leu His Glu Lys Asp Ser Glu Ser Gly Gly Gly
1155 1160 1165

Lys Asp
1170

( 2 ) INFORMATION FOR SEQ ID NO:3:

( i ) SEQUENCE CHARACTERISTICS:
( A ) LENGTH: 531 amino acids
( B ) TYPE: amino acid
( D ) TOPOLOGY: both ( i i ) MOLECULE TYPE: protein ( v i ) ORIGINAL SOURCE:
( A ) ORGANISM: Homo sapiens
( G ) CELL TYPE: T-cell
( H ) CELL LINE: HL-60

( i x ) FEATURE:
( A ) NAME/KEY: Region
( B ) LOCATION: 1..25
( D ) OTHER INFORMATION: /label=Signal
/ note= "Signal sequence"

( i x ) FEATURE:
( A ) NAME/KEY: Region
( B ) LOCATION: 41..100
( D ) OTHER INFORMATION: /label=Ig1

( i x ) FEATURE:
( A ) NAME/KEY: Region
( B ) LOCATION: 128..190
( D ) OTHER INFORMATION: /label=Ig2

( i x ) FEATURE:
( A ) NAME/KEY: Region ( B ) LOCATION: 230..294
( D ) OTHER INFORMATION: /label=Ig3

( i x ) FEATURE:
( A ) NAME/KEY: Region
( B ) LOCATION: 325..375
( D ) OTHER INFORMATION: /label=Ig4

( i x ) FEATURE:
( A ) NAME/KEY: Region
( B ) LOCATION: 413..461
( D ) OTHER INFORMATION: /label=Ig5

( i x ) FEATURE:
( A ) NAME/KEY: Duplication
( B ) LOCATION: 481..503
( D ) OTHER INFORMATION: /label=Trans
/ note= "Transmembrane domain"

( i x ) FEATURE:
( A ) NAME/KEY: Binding-site
( B ) LOCATION: 152..154
( D ) OTHER INFORMATION: /label=Attachment
/ note= "Cell attachment site"

( x ) PUBLICATION INFORMATION:
( A ) AUTHORS: Pigott,
Power,
( B ) TITLE: ICAM-1 Amino acid sequence (from HL-60)
( C ) JOURNAL: The Adhesion Molecule Facts Book
( F ) PAGES: 75-75
( G ) DATE: 1993
( K ) RELEVANT RESIDUES IN SEQ ID NO:3: FROM 1 TO 531

( x i ) SEQUENCE DESCRIPTION: SEQ ID NO:3:

| | | | | | | | | | | | | | | | |
|---|---|---|---|---|---|---|---|---|---|---|---|---|---|---|---|
| Met | Ala | Pro | Ser | Ser | Pro | Arg | Pro | Ala | Leu | Pro | Ala | Leu | Leu | Val | Leu |
| 1 | | | | 5 | | | | | 10 | | | | | 15 | |
| Leu | Gly | Ala | Leu | Phe | Pro | Gly | Pro | Gly | Asn | Ala | Gln | Thr | Ser | Val | Ser |
| | | | 20 | | | | | 25 | | | | | 30 | | |
| Pro | Ser | Lys | Val | Ile | Leu | Pro | Arg | Gly | Gly | Ser | Val | Leu | Val | Thr | Cys |
| | | 35 | | | | | 40 | | | | | 45 | | | |
| Ser | Thr | Ser | Cys | Asp | Gln | Pro | Lys | Leu | Leu | Gly | Ile | Glu | Thr | Pro | Leu |
| | 50 | | | | | 55 | | | | | 60 | | | | |
| Pro | Lys | Lys | Glu | Leu | Leu | Leu | Pro | Gly | Asn | Asn | Arg | Lys | Val | Tyr | Glu |
| 65 | | | | | 70 | | | | | 75 | | | | | 80 |
| Leu | Ser | Asn | Val | Gln | Glu | Asp | Ser | Gln | Pro | Met | Cys | Tyr | Ser | Asn | Cys |
| | | | | 85 | | | | | 90 | | | | | 95 | |
| Pro | Asp | Gly | Ser | Thr | Ala | Lys | Thr | Phe | Leu | Thr | Val | Tyr | Trp | Thr | Pro |
| | | | 100 | | | | | 105 | | | | | 110 | | |
| Glu | Arg | Val | Glu | Leu | Ala | Pro | Leu | Pro | Ser | Trp | Gln | Pro | Val | Gly | Lys |
| | | 115 | | | | | 120 | | | | | 125 | | | |
| Asn | Leu | Thr | Leu | Arg | Cys | Gln | Val | Glu | Gly | Gly | Ala | Pro | Arg | Ala | Asn |
| | 130 | | | | | 135 | | | | | 140 | | | | |
| Leu | Thr | Val | Val | Leu | Leu | Arg | Gly | Glu | Lys | Glu | Leu | Lys | Arg | Glu | Pro |
| 145 | | | | | 150 | | | | | 155 | | | | | 160 |
| Ala | Val | Gly | Glu | Pro | Ala | Glu | Val | Thr | Thr | Thr | Val | Leu | Val | Arg | Arg |
| | | | | 165 | | | | | 170 | | | | | 175 | |
| Asp | His | His | Gly | Ala | Asn | Phe | Ser | Cys | Arg | Thr | Glu | Leu | Asp | Leu | Arg |
| | | | 180 | | | | | 185 | | | | | 190 | | |
| Pro | Gln | Gly | Leu | Glu | Leu | Phe | Glu | Asn | Thr | Ser | Ala | Pro | Tyr | Gln | Leu |
| | | 195 | | | | | 200 | | | | | 205 | | | |
| Gln | Thr | Phe | Val | Leu | Pro | Ala | Thr | Pro | Pro | Gln | Leu | Val | Ser | Pro | Arg |
| | 210 | | | | | 215 | | | | | 220 | | | | |
| Val | Leu | Glu | Val | Asp | Thr | Gln | Gly | Thr | Val | Val | Cys | Ser | Leu | Asp | Gly |
| 225 | | | | | 230 | | | | | 235 | | | | | 240 |

-continued

Leu Phe Pro Val Ser Glu Ala Gln Val His Leu Ala Leu Gly Asp Gln
245 250 255

Arg Leu Asn Pro Thr Val Thr Tyr Gly Asn Asp Ser Phe Ser Ala Lys
260 265 270

Ala Ser Val Ser Val Thr Ala Glu Asp Glu Gly Thr Gln Arg Leu Thr
275 280 285

Cys Ala Val Ile Ile Gly Asn Gln Ser Gln Glu Thr Leu Gln Thr Val
290 295 300

Thr Ile Tyr Ser Phe Pro Ala Pro Asn Val Ile Leu Thr Lys Pro Glu
305 310 315 320

Val Ser Glu Gly Thr Glu Val Thr Val Lys Cys Glu Ala His Pro Arg
325 330 335

Ala Lys Val Thr Leu Asn Gly Val Pro Ala Gln Pro Leu Gly Pro Arg
340 345 350

Ala Gln Leu Leu Leu Lys Ala Thr Pro Glu Asp Asn Gly Arg Ser Phe
355 360 365

Ser Cys Ser Ala Thr Leu Glu Val Ala Gly Gln Leu Ile His Lys Asn
370 375 380

Gln Thr Arg Glu Leu Arg Val Leu Tyr Gly Pro Arg Leu Asp Glu Arg
385 390 395 400

Asp Cys Pro Gly Asn Trp Thr Trp Pro Glu Asn Ser Gln Gln Thr Pro
405 410 415

Met Cys Gln Ala Trp Gly Asn Pro Leu Pro Glu Leu Lys Cys Leu Lys
420 425 430

Asp Gly Thr Phe Pro Leu Pro Ile Gly Glu Ser Val Thr Val Thr Arg
435 440 445

Asp Leu Glu Gly Thr Tyr Leu Cys Arg Ala Arg Ser Thr Gln Gly Glu
450 455 460

Val Thr Arg Glu Val Thr Val Asn Val Leu Ser Pro Arg Tyr Glu Ile
465 470 475 480

Val Ile Ile Thr Val Val Ala Ala Ala Val Ile Met Gly Thr Ala Gly
485 490 495

Leu Ser Thr Tyr Leu Tyr Asn Arg Gln Arg Lys Ile Lys Lys Tyr Arg
500 505 510

Leu Gln Gln Ala Gln Lys Gly Thr Pro Met Lys Pro Asn Thr Gln Ala
515 520 525

Thr Pro Pro
530

( 2 ) INFORMATION FOR SEQ ID NO:4:

( i ) SEQUENCE CHARACTERISTICS:
( A ) LENGTH: 21 amino acids
( B ) TYPE: amino acid
( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
( A ) ORGANISM: Homo sapiens
( G ) CELL TYPE: T-cell
( H ) CELL LINE: HL-60

( x i ) SEQUENCE DESCRIPTION: SEQ ID NO:4:

Gln Thr Ser Val Ser Pro Ser Lys Val Ile Leu Pro Arg Gly Gly Ser

-continued 1 5 10 15

Val Leu Val Thr Gly
20

( 2 ) INFORMATION FOR SEQ ID NO:5:

( i ) SEQUENCE CHARACTERISTICS:
( A ) LENGTH: 22 amino acids
( B ) TYPE: amino acid
( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
( A ) ORGANISM: Homo sapiens
( G ) CELL TYPE: T-cell
( H ) CELL LINE: HL-60

( x i ) SEQUENCE DESCRIPTION: SEQ ID NO:5:

Xaa Gln Thr Ser Val Ser Pro Ser Lys Val Ile Leu Pro Arg Gly Gly
1 5 10 15

Ser Val Leu Val Thr Gly
20

( 2 ) INFORMATION FOR SEQ ID NO:6:

( i ) SEQUENCE CHARACTERISTICS:
( A ) LENGTH: 21 amino acids
( B ) TYPE: amino acid
( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
( A ) ORGANISM: Homo sapiens
( G ) CELL TYPE: T-cell
( H ) CELL LINE: HL-60

( x i ) SEQUENCE DESCRIPTION: SEQ ID NO:6:

Gln Thr Ser Val Ser Pro Ser Lys Val Ile Leu Pro Arg Gly Gly Ser
1 5 10 15

Val Leu Val Thr Gly
20

( 2 ) INFORMATION FOR SEQ ID NO:7:

( i ) SEQUENCE CHARACTERISTICS:
( A ) LENGTH: 12 amino acids
( B ) TYPE: amino acid
( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
( A ) ORGANISM: Homo sapiens
( G ) CELL TYPE: T-cell
( H ) CELL LINE: HL-60

( x i ) SEQUENCE DESCRIPTION: SEQ ID NO:7:

Cys Leu Pro Arg Gly Gly Ser Val Leu Val Thr Cys
1 5 10

( 2 ) INFORMATION FOR SEQ ID NO:8:

( i ) SEQUENCE CHARACTERISTICS:
( A ) LENGTH: 12 amino acids
( B ) TYPE: amino acid
( D ) TOPOLOGY: cyclic ( i i ) MOLECULE TYPE: peptide ( i i i ) HYPOTHETICAL: NO ( v ) FRAGMENT TYPE: internal ( v i ) ORIGINAL SOURCE:
( A ) ORGANISM: Homo sapiens
( G ) CELL TYPE: T-cell
( H ) CELL LINE: HL-60

( x i ) SEQUENCE DESCRIPTION: SEQ ID NO:8:

Cys Leu Pro Arg Gly Gly Ser Val Leu Val Thr Cys
1 5 10

( 2 ) INFORMATION FOR SEQ ID NO:9:

( i ) SEQUENCE CHARACTERISTICS:
( A ) LENGTH: 11 amino acids
( B ) TYPE: amino acid
( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
( A ) ORGANISM: Homo sapiens
( G ) CELL TYPE: T-cell
( H ) CELL LINE: HL-60

( x i ) SEQUENCE DESCRIPTION: SEQ ID NO:9:

Leu Pro Arg Gly Gly Ser Val Leu Val Thr Gly
1 5 10

( 2 ) INFORMATION FOR SEQ ID NO:10:

( i ) SEQUENCE CHARACTERISTICS:
( A ) LENGTH: 10 amino acids
( B ) TYPE: amino acid
( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
( A ) ORGANISM: Homo sapiens
( G ) CELL TYPE: T-cell
( H ) CELL LINE: HL-60

( x i ) SEQUENCE DESCRIPTION: SEQ ID NO:10:

Gln Thr Ser Val Ser Pro Ser Lys Val Ile
1 5 10

( 2 ) INFORMATION FOR SEQ ID NO:11:

( i ) SEQUENCE CHARACTERISTICS:
( A ) LENGTH: 25 amino acids ( B ) TYPE: amino acid
( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
( A ) ORGANISM: Homo sapiens
( G ) CELL TYPE: T-cell
( H ) CELL LINE: HL-60

( x i ) SEQUENCE DESCRIPTION: SEQ ID NO:11:

Asp Gln Pro Lys Leu Leu Gly Ile Glu Thr Pro Leu Pro Lys Lys Glu
1 5 10 15

Leu Leu Leu Pro Gly Asn Asn Arg Lys
20 25

( 2 ) INFORMATION FOR SEQ ID NO:12:

( i ) SEQUENCE CHARACTERISTICS:
( A ) LENGTH: 24 amino acids
( B ) TYPE: amino acid
( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
( A ) ORGANISM: Homo sapiens
( F ) TISSUE TYPE: tonsil ( x i ) SEQUENCE DESCRIPTION: SEQ ID NO:12:

Lys Glu Leu Leu Leu Pro Gly Asn Asn Arg Lys Val Tyr Glu Leu Ser
1 5 10 15

Asn Val Gln Glu Asp Ser Gln Pro
20

( 2 ) INFORMATION FOR SEQ ID NO:13:

( i ) SEQUENCE CHARACTERISTICS:
( A ) LENGTH: 10 amino acids
( B ) TYPE: amino acid
( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
( A ) ORGANISM: Homo sapiens
( G ) CELL TYPE: T-cell
( H ) CELL LINE: HL-60

( x i ) SEQUENCE DESCRIPTION: SEQ ID NO:13:

Pro Ser Lys Val Ile Leu Pro Arg Gly Gly
1 5 10

( 2 ) INFORMATION FOR SEQ ID NO:14:

( i ) SEQUENCE CHARACTERISTICS:
( A ) LENGTH: 12 amino acids
( B ) TYPE: amino acid
( D ) TOPOLOGY: linear (ii) MOLECULE TYPE: peptide (iii) HYPOTHETICAL: NO (v) FRAGMENT TYPE: internal (vi) ORIGINAL SOURCE:
(A) ORGANISM: Homo sapiens
(G) CELL TYPE: T-cell
(H) CELL LINE: HL-60

(xi) SEQUENCE DESCRIPTION: SEQ ID NO:14:

Xaa Pro Ser Lys Val Ile Leu Pro Arg Gly Gly Cys
1 5 10

(2) INFORMATION FOR SEQ ID NO:15:

(i) SEQUENCE CHARACTERISTICS:
(A) LENGTH: 12 amino acids
(B) TYPE: amino acid
(D) TOPOLOGY: cyclic (ii) MOLECULE TYPE: peptide (iii) HYPOTHETICAL: NO (v) FRAGMENT TYPE: internal (vi) ORIGINAL SOURCE:
(A) ORGANISM: Homo sapiens
(G) CELL TYPE: T-cell
(H) CELL LINE: HL-60

(xi) SEQUENCE DESCRIPTION: SEQ ID NO:15:

Xaa Pro Ser Lys Val Ile Leu Pro Arg Gly Gly Cys
1 5 10

(2) INFORMATION FOR SEQ ID NO:16:

(i) SEQUENCE CHARACTERISTICS:
(A) LENGTH: 25 amino acids
(B) TYPE: amino acid
(D) TOPOLOGY: linear (ii) MOLECULE TYPE: peptide (iii) HYPOTHETICAL: NO (v) FRAGMENT TYPE: internal (vi) ORIGINAL SOURCE:
(A) ORGANISM: Homo sapiens
(F) TISSUE TYPE: tonsil (xi) SEQUENCE DESCRIPTION: SEQ ID NO:16:

Asp Leu Ser Tyr Ser Leu Asp Asp Leu Arg Asn Val Lys Lys Leu Gly
1 5 10 15

Gly Asp Leu Leu Arg Ala Leu Asn Glu
20 25

(2) INFORMATION FOR SEQ ID NO:17:

(i) SEQUENCE CHARACTERISTICS:
(A) LENGTH: 24 amino acids
(B) TYPE: amino acid
(D) TOPOLOGY: linear (ii) MOLECULE TYPE: peptide (iii) HYPOTHETICAL: NO (v) FRAGMENT TYPE: internal -continued ( v i ) ORIGINAL SOURCE:
( A ) ORGANISM: Homo sapiens
( G ) CELL TYPE: T-cell
( H ) CELL LINE: HL-60

( x i ) SEQUENCE DESCRIPTION: SEQ ID NO:17:

```
Gly Val Asp Val Asp Gln Asp Gly Glu Thr Glu Leu Ile Gly Ala Pro
1               5                   10                  15

Leu Phe Tyr Gly Glu Gln Arg Gly
            20
```

( 2 ) INFORMATION FOR SEQ ID NO:18:

( i ) SEQUENCE CHARACTERISTICS:
( A ) LENGTH: 24 amino acids
( B ) TYPE: amino acid
( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
( A ) ORGANISM: Homo sapiens
( G ) CELL TYPE: T-cell
( H ) CELL LINE: HL-60

( x i ) SEQUENCE DESCRIPTION: SEQ ID NO:18:

```
Ile Thr Asp Gly Glu Ala Thr Asp Ser Gly Asn Ile Asp Ala Ala Lys
1               5                   10                  15

Asp Ile Ile Tyr Ile Ile Gly Ile
            20
```

( 2 ) INFORMATION FOR SEQ ID NO:19:

( i ) SEQUENCE CHARACTERISTICS:
( A ) LENGTH: 24 amino acids
( B ) TYPE: amino acid
( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
( A ) ORGANISM: Homo sapiens
( G ) CELL TYPE: T-cell
( H ) CELL LINE: HL-60

( x i ) SEQUENCE DESCRIPTION: SEQ ID NO:19:

```
Ile Thr Asp Gly Glu Ala Thr Asp Ser Gly Asn Ile Asp Ala Ala Lys
1               5                   10                  15

Asp Ile Ile Tyr Ile Ile Gly Ile
            20
```